(12) United States Patent
Kobayashi et al.

(10) Patent No.: US 12,067,802 B2
(45) Date of Patent: Aug. 20, 2024

(54) IMAGING DEVICE AND AUTHENTICATION DEVICE

(71) Applicant: SEMICONDUCTOR ENERGY LABORATORY CO., LTD., Atsugi (JP)

(72) Inventors: Hidetomo Kobayashi, Kanagawa (JP); Takayuki Ikeda, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 779 days.

(21) Appl. No.: 17/282,119

(22) PCT Filed: Oct. 1, 2019

(86) PCT No.: PCT/IB2019/058321
§ 371 (c)(1),
(2) Date: Apr. 1, 2021

(87) PCT Pub. No.: WO2020/075002
PCT Pub. Date: Apr. 16, 2020

(65) Prior Publication Data
US 2021/0374378 A1 Dec. 2, 2021

(30) Foreign Application Priority Data
Oct. 11, 2018 (JP) .................................. 2018-192829

(51) Int. Cl.
*H01L 27/146* (2006.01)
*A61B 5/00* (2006.01)
(Continued)

(52) U.S. Cl.
CPC .... *G06V 40/1318* (2022.01); *H01L 27/14603* (2013.01); *H01L 27/14621* (2013.01); *H01L 27/14623* (2013.01); *H01L 27/14649* (2013.01)

(58) Field of Classification Search
CPC ................ G06V 40/1318; G06V 40/14; H01L 27/14603; H01L 27/14621;
(Continued)

(56) References Cited

U.S. PATENT DOCUMENTS 9,155,498 B2   10/2015   Akiyama
9,167,994 B2   10/2015   Akiyama
(Continued)

FOREIGN PATENT DOCUMENTS

CN   103022072 A   4/2013
CN   104051494 A   9/2014
(Continued)

OTHER PUBLICATIONS

International Search Report (Application No. PCT/IB2019/058321) Dated Dec. 24, 2019.
Written Opinion (Application No. PCT/IB2019/058321) Dated Dec. 24, 2019.
Chinese Office Action (Application No. 201980066810.8) Dated Feb. 8, 2024.

*Primary Examiner* — Asghar H Bilgrami
(74) *Attorney, Agent, or Firm* — Fish & Richardson P.C.

(57) ABSTRACT

A highly convenient imaging device is provided. Alternatively, a highly reliable imaging device is provided. Alternatively, a highly convenient authentication device is provided. Alternatively, a highly reliable authentication device is provided. The imaging device includes a substrate, a pixel array, and an adhesive layer. The substrate has flexibility, the pixel array is positioned over a first surface of the substrate, and the adhesive layer is positioned on a second surface facing the first surface of the substrate. The pixel array includes a light-receiving element and a light-emitting element. The light-receiving element has a function of sensing infrared light and includes a first pixel electrode, an active layer, and a common electrode. The light-emitting element has a function of emitting infrared light and includes a second pixel electrode, a light-emitting layer, and the com-
(Continued)

mon electrode. The active layer is positioned over the first pixel electrode and contains a first organic compound. The light-emitting layer is positioned over the second pixel electrode and contains a second organic compound different from the first organic compound. The common electrode includes a portion overlapping with the first pixel electrode with the active layer therebetween, and a portion overlapping with the second pixel electrode with the light-emitting layer therebetween.

8 Claims, 19 Drawing Sheets

(51) Int. Cl.
  *G06V 40/13* (2022.01)
  *H04N 25/76* (2023.01)
(58) Field of Classification Search
  CPC ......... H01L 27/14623; H01L 27/14649; H01L 27/14678; A61B 2562/0233; A61B 5/0002; A61B 5/0059; A61B 5/7225; A61B 2562/046; A61B 5/489; A61B 5/6825; A61B 5/1171; Y02E 10/549; H04N 25/76; H04N 5/33; H10K 65/00; H10K 59/60; H10K 50/00; H10K 77/111
  See application file for complete search history.

(56) References Cited

U.S. PATENT DOCUMENTS

| | | | |
|---|---|---|---|
| 2009/0302755 | A1* | 12/2009 | Racine ................. H10K 50/828 |
| | | | 313/505 |
| 2011/0108836 | A1 | 5/2011 | Koyama et al. |
| 2013/0075761 | A1 | 3/2013 | Akiyama |
| 2013/0285046 | A1* | 10/2013 | Yamazaki ........... H01L 29/7869 |
| | | | 257/43 |
| 2020/0013993 | A1* | 1/2020 | Defranco ............... H10K 50/30 |

FOREIGN PATENT DOCUMENTS

| | | | |
|---|---|---|---|
| CN | 105574479 | A | 5/2016 |
| JP | 2007-081203 | A | 3/2007 |
| JP | 2007-122164 | A | 5/2007 |
| JP | 2011-119711 | A | 6/2011 |
| JP | 2013-073965 | A | 4/2013 |
| JP | 2013073965 | * | 4/2013 |
| JP | 2013-243355 | A | 12/2013 |
| JP | 2017-220604 | A | 12/2017 |
| JP | 2018-174246 | A | 11/2018 |
| KR | 2013-0033278 | A | 4/2013 |
| TW | 201316495 | | 4/2013 |
| WO | WO-2018/180577 | | 10/2018 |
| WO | WO-2020/053692 | | 3/2020 |

* cited by examiner

FIG. 8A

| Line[1] | Rn-1 | En | | Rn | En+1 | |
|---|---|---|---|---|---|---|
| Line[2] | En-1 | Rn-1 | En | | Rn | En+1 |
| Line[3] | En-1 | | Rn-1 | En | | Rn | En+1 |
| ⋮ | | | | | | |
| Line[M] | En-1 | | Rn-1 | En | | Rn |

FIG. 8B

| Line[1] | En | Rn | | | En+1 |
|---|---|---|---|---|---|
| Line[2] | En | | Rn | | En+1 |
| Line[3] | En | | | Rn | En+1 |
| ⋮ | | | | | |
| Line[M] | En | | | Rn | En+1 |

FIG. 14A1
FIG. 14A2
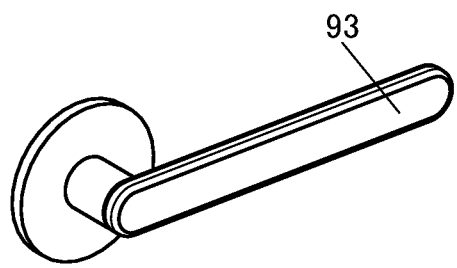
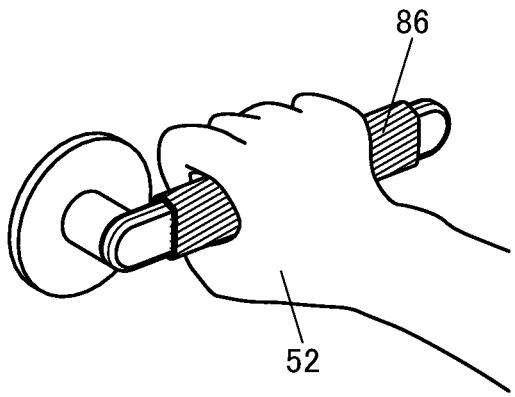
FIG. 14B1
FIG. 14B2
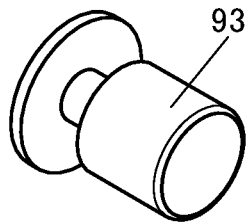
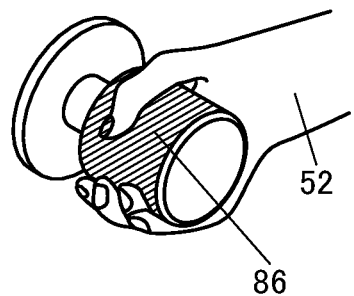
FIG. 14C
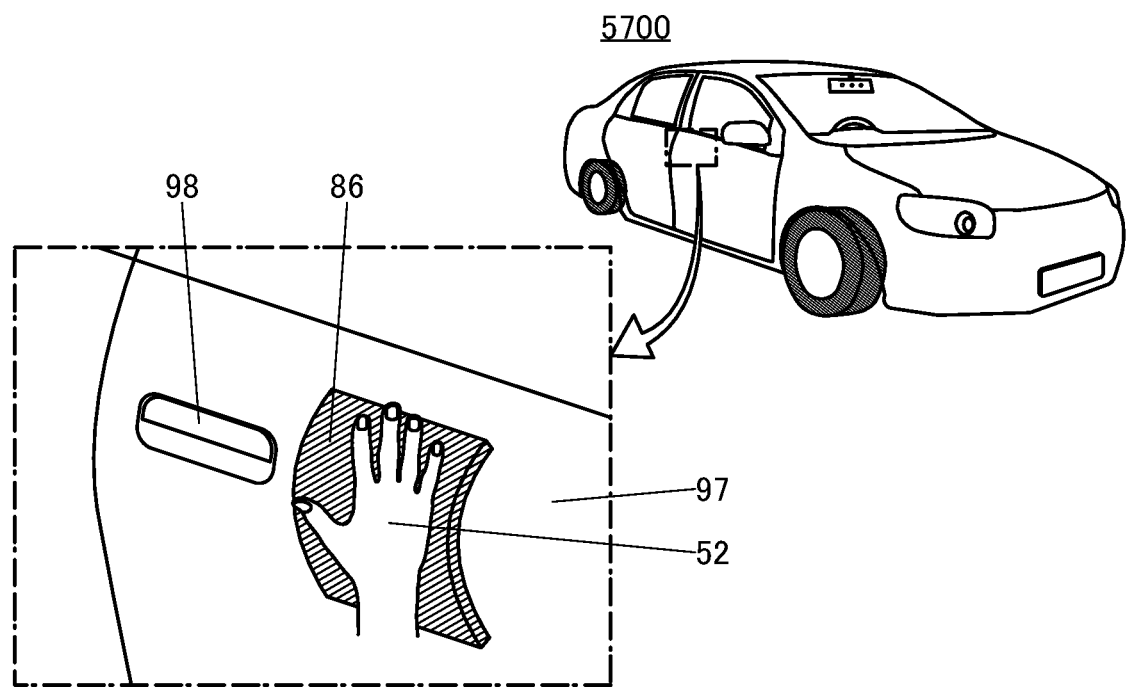

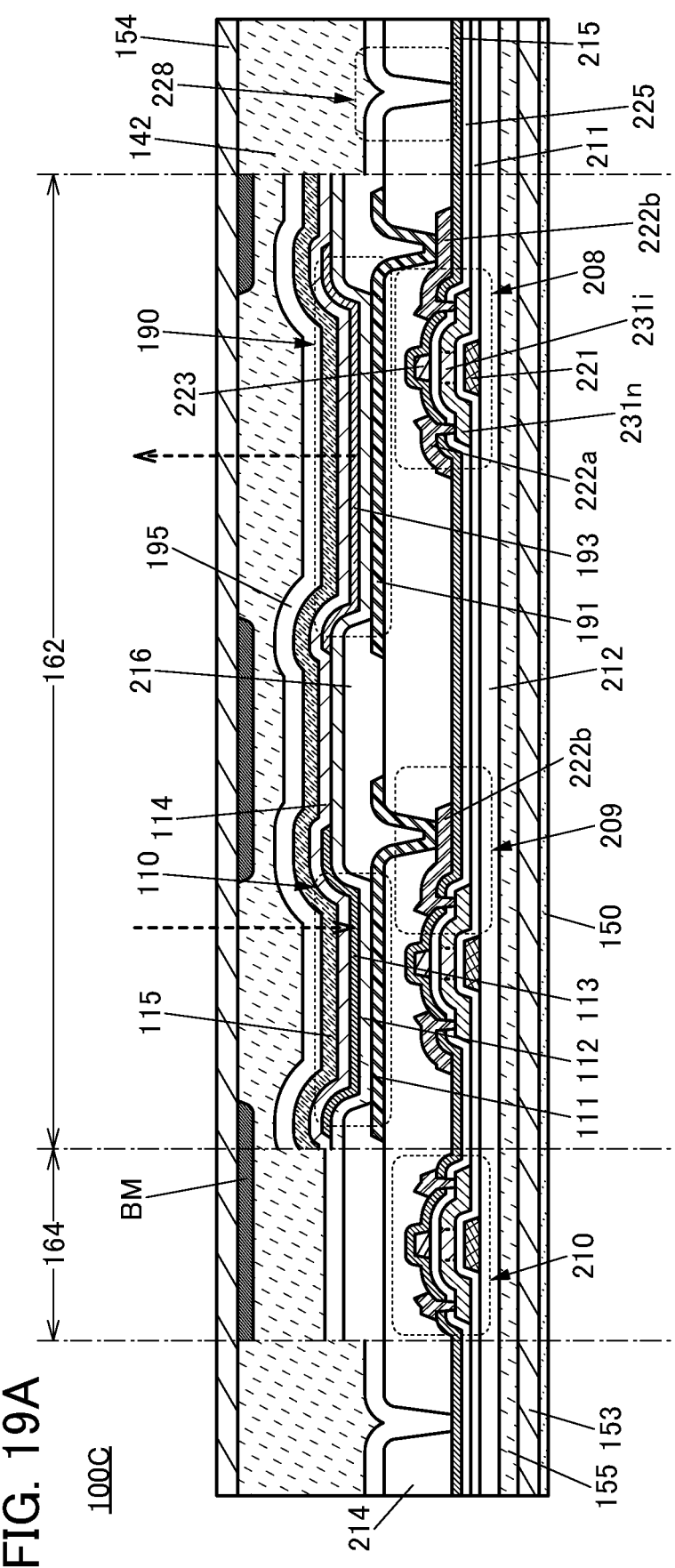
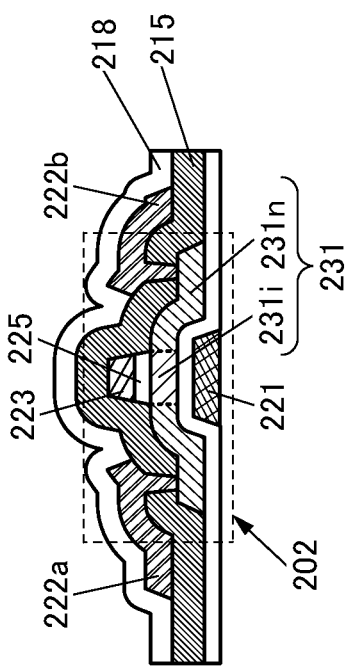
FIG. 19A
FIG. 19B

IMAGING DEVICE AND AUTHENTICATION DEVICE

CROSS REFERENCE TO RELATED APPLICATIONS

This application is a U.S. National Phase Application under 35 U.S.C. § 371 of International Application PCT/IB2019/058321, filed on Oct. 1, 2019, which is incorporated by reference and claims the benefit of a foreign priority application filed in Japan on Oct. 11, 2018, as Application No. 2018-192829.

TECHNICAL FIELD

One embodiment of the present invention relates to an imaging device and an authentication device.

Note that one embodiment of the present invention is not limited to the above technical field. Examples of the technical field of one embodiment of the present invention disclosed in this specification and the like include a semiconductor device, a display device, a light-emitting device, a power storage device, a memory device, an electronic device, a lighting device, an input device, an input/output device, a driving method thereof, and a manufacturing method thereof. A semiconductor device generally means a device that can function by utilizing semiconductor characteristics.

BACKGROUND ART

Imaging devices have been mounted in devices such as digital cameras conventionally, and with the widespread use of portable information terminals such as smartphones and tablet terminals, an improvement in performance, a reduction in size, and a reduction in costs have been needed. Moreover, imaging devices have been not only used for taking a photograph or a moving image but also applied to biological authentication such as face authentication, fingerprint authentication, and vein authentication or input devices such as touch sensors or motion sensors, for example; that is, the usage has been diversified.

In addition, improvement in performance and function of an imaging device has progressed. Patent Document 1 discloses, for example, an imaging device in which a transistor including an oxide semiconductor and having an extremely low off-state current is used in part of a pixel circuit and a transistor including silicon with which a CMOS (Complementary Metal Oxide Semiconductor) circuit can be formed is used in a peripheral circuit.

Patent Document 2 discloses an imaging device in which a transistor including silicon, a transistor including an oxide semiconductor, and a photodiode including a crystalline silicon layer are stacked.

REFERENCE

Patent Document

[Patent Document 1]
[Patent Document 1] Japanese Published Patent Application No. 2011-119711
[Patent Document 2]
[Patent Document 2] Japanese Published Patent Application No. 2013-243355

SUMMARY OF THE INVENTION

Problems to be Solved by the Invention

An object of one embodiment of the present invention is to provide a highly convenient imaging device. Alternatively, an object is to provide a highly reliable imaging device. Alternatively, an object is to provide a novel imaging device. Alternatively, an object is to provide a display device having high reliability. Alternatively, an object is to provide a highly reliable authentication device. Alternatively, an object is to provide a novel authentication device.

Note that the description of these objects does not preclude the existence of other objects. One embodiment of the present invention does not have to achieve all these objects. Note that objects other than these can be derived from the description of the specification, the drawings, the claims, and the like.

Means for Solving the Problems

One embodiment of the present invention is an imaging device including a substrate, a pixel array, and an adhesive layer. The substrate has flexibility. The pixel array is positioned over a first surface of the substrate. The adhesive layer is positioned on a second surface facing the first surface of the substrate. The pixel array includes a light-receiving element and a light-emitting element. The light-receiving element has a function of sensing infrared light and includes a first pixel electrode, an active layer, and a common electrode. The light-emitting element has a function of emitting infrared light and includes a second pixel electrode, a light-emitting layer, and the common electrode. The active layer is positioned over the first pixel electrode and contains a first organic compound. The light-emitting layer is positioned over the second pixel electrode and contains a second organic compound different from the first organic compound. The common electrode includes a portion overlapping with the first pixel electrode with the active layer therebetween, and a portion overlapping with the second pixel electrode with the light-emitting layer therebetween.

One embodiment of the present invention is an imaging device including a substrate, a pixel array, and an adhesive layer. The substrate has flexibility. The pixel array is positioned over a first surface of the substrate, and the adhesive layer is positioned on a second surface facing the first surface of the substrate. The pixel array includes a light-receiving element and a light-emitting element. The light-receiving element has a function of sensing infrared light and includes a first pixel electrode, a common layer, an active layer, and a common electrode. The light-emitting element has a function of emitting infrared light and includes a second pixel electrode, the common layer, a light-emitting layer, and the common electrode. The active layer is positioned over the first pixel electrode and contains a first organic compound. The light-emitting layer is positioned over the second pixel electrode and contains a second organic compound different from the first organic compound. The common layer is positioned over the first pixel electrode and the second pixel electrode, and include a portion overlapping with the active layer and a portion overlapping with the light-emitting layer. The common electrode includes a portion overlapping with the first pixel electrode with the common layer and the active layer therebetween, and a portion overlapping with the second pixel electrode with the common layer and the light-emitting layer therebetween.

In the above imaging device, the pixel array preferably includes at least one of a transistor including a metal oxide in a channel formation region and a transistor including silicon in a channel formation region.

One embodiment of the present invention is an authentication device including the above-described imaging device, a control portion, a memory portion, and an input/output portion, where the control portion, the memory portion, and the input/output portion are positioned over the first surface of the substrate, where the imaging device has a function of capturing an image, where the memory portion has a function of storing a registered image, where the control portion has a function of comparing the image and the registered image, where the input/output portion includes an antenna, and where the input/output portion has a function of outputting a comparison result to the outside and a function of receiving power wirelessly.

In the above-described authentication device, it is preferable that an external driver circuit be further included, that the external driver circuit be not in contact with the substrate, and that the input/output portion have a function of outputting the comparison result to the external driver circuit.

Effect of the Invention

According to one embodiment of the present invention, a highly convenient imaging device can be provided. Alternatively, a highly reliable imaging device can be provided. Alternatively, a novel imaging device can be provided. Alternatively, a highly convenient authentication device can be provided. Alternatively, a highly reliable authentication device can be provided. Alternatively, a novel authentication device can also be provided.

Note that the description of the effects does not preclude the existence of other effects. Note that one embodiment of the present invention does not need to have all these effects. Note that effects other than these can be derived from the description of the specification, the drawings, the claims, and the like.

BRIEF DESCRIPTION OF THE DRAWINGS

FIG. 8A is a diagram showing a rolling shutter mode. FIG. 8B is a diagram showing a global shutter mode.

FIG. 14A1 and FIG. 14B1 each illustrate an example of a door knob. FIG. 14A2, FIG. 14B2, and FIG. 14C are perspective views each illustrating an example of an authentication device.

FIG. 19A and FIG. 19B are cross-sectional views illustrating an example of an authentication device.

MODE FOR CARRYING OUT THE INVENTION

Figure 1A:
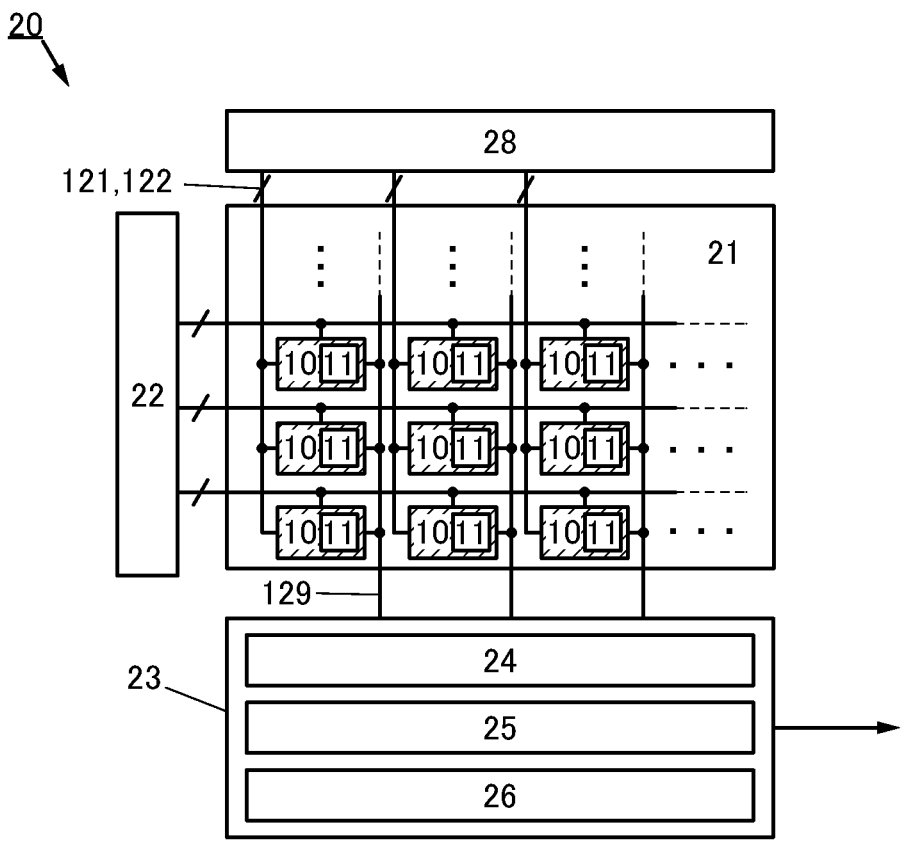
FIG. 1A is a block diagram illustrating an imaging device.

Hereinafter, embodiments will be described with reference to the drawings. Note that the embodiments can be implemented with many different modes, and it will be readily understood by those skilled in the art that modes and details thereof can be changed in various ways without departing from the spirit and scope thereof. Thus, the present invention should not be construed as being limited to the following description of the embodiments.

Note that in structures of the present invention described below, the same portions or portions having similar functions are denoted by the same reference numerals in different drawings, and a description thereof is not repeated. Furthermore, the same hatch pattern is used for the portions having similar functions, and the portions are not especially denoted by reference numerals in some cases.

Even in the case where a single component is illustrated in a circuit diagram, the component may be composed of a plurality of parts as long as there is no functional inconvenience. For example, in some cases, a plurality of transistors that operate as switches are connected in series or in parallel. In some cases, capacitors may be separately arranged in a plurality of positions.

One conductor has a plurality of functions such as a wiring, an electrode, and a terminal in some cases. In this specification, a plurality of names are used for the same component in some cases. Even in the case where components are illustrated in a circuit diagram as if they were directly connected to each other, the components may actually be connected to each other through a plurality of conductors; in this specification, even such a structure is included in direct connection.

Note that in each drawing described in this specification, the size, the layer thickness, or the region of each component is exaggerated for clarity in some cases. Therefore, they are not limited to the illustrated scale.

Note that in this specification and the like, the ordinal numbers such as "first" and "second" are used in order to avoid confusion among components and do not limit the number.

Embodiment 1

In this embodiment, an imaging device of one embodiment of the present invention is described with reference to FIG. 1 to FIG. 10.

One embodiment of the present invention is an imaging device including a light-emitting element. Light emitted from the light-emitting element and reflected by an object is received by a light-receiving element included in a pixel circuit.

With use of a light-emitting element emitting light whose wavelength is in the infrared range (hereinafter referred to as infrared light), usage for biometric authentication or failure analysis of industrial products becomes possible. Furthermore, with use of a pixel circuit which can capture images with the global shutter mode, undistorted images can be obtained even if the object is moving.

In this specification and the like, infrared light refers to light with a wavelength greater than or equal to 0.7 μm and less than or equal to 1000 μm, for example. In addition, near infrared light with a wavelength greater than or equal to 0.7 μm and less than or equal to 2.5 μm is simply referred to as infrared light in some cases.

FIG. 1A is a block diagram illustrating an imaging device 20 of one embodiment of the present invention. The imaging device 20 includes a pixel array 21 including pixel circuits 10 arranged in a matrix, a circuit 22 having a function of selecting a row of the pixel array 21 (row driver), a circuit 23 having a function of reading out data from the pixel circuits 10, and a circuit 28 supplying a power supply potential. The pixel circuits 10 each include a light-emitting element 11.

The circuit 23 can include a circuit 24 having a function of selecting a column of the pixel array 21 (column driver), a circuit 25 for performing correlated double sampling processing on output data from the pixel circuits 10 (CDS circuit), a circuit 26 having a function of converting analog data output from the circuit 25 into digital data (A/D converter circuit or the like), and the like.

Figure 1B:
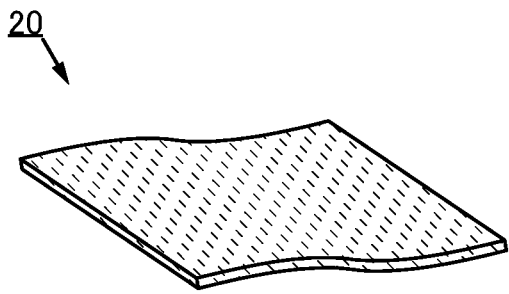
FIG. 1B and FIG. 1C are perspective views illustrating the imaging device.

An example of an external view of the imaging device 20 is shown. FIG. 1B is a perspective view of the imaging device 20. The imaging device 20 has a sheet-like shape and further has flexibility as shown in FIG. 1B. The imaging device 20 having flexibility can be provided for an object having a curved surface, such as a door knob or a steering wheel of an automobile. One embodiment of the present invention can be a highly convenient imaging device that can be used for a variety of applications when having flexibility.

Figure 1C:
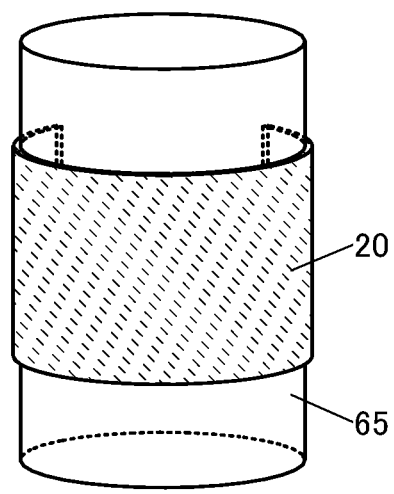

The imaging device 20 includes an adhesive layer (not illustrated) on its surface, and the imaging device 20 can be fixed to an object with the adhesive layer. FIG. 1C shows an example in which the imaging device 20 is provided on a curved surface of a cylindrical object 65. One embodiment of the present invention can be a highly convenient imaging device that can be fixed to the existing object with the adhesive layer.

Figure 2A:
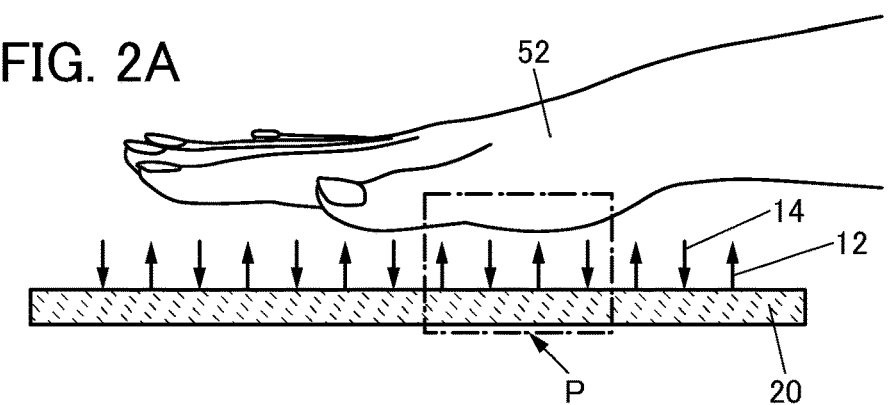
FIG. 2A and FIG. 2B are diagrams illustrating an imaging device.

The imaging device of one embodiment of the present invention has a function of emitting infrared light to an imaging object close to or in contact with the imaging device and sensing infrared light entering the imaging device to capture an image of the imaging object. FIG. 2A is an external view for capturing an image with use of the imaging device 20. For example, as illustrated in FIG. 2A, a hand 52 close to and over the imaging device 20 is irradiated with infrared light 12, and infrared light 14 entering the imaging device 20 from the hand 52 is sensed, so that an image is captured. The imaging device 20 can be referred to as a reflective imaging device.

Figure 2B:
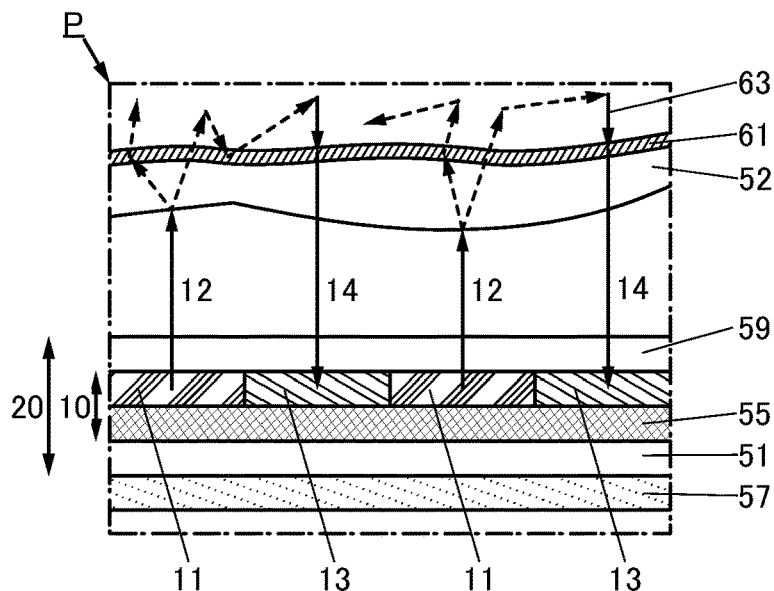

An enlarged view of a portion P surrounded by a dashed line in FIG. 2A is shown in FIG. 2B. FIG. 2B is a schematic cross-sectional view of the pixel array 21 included in the imaging device 20. The pixel array 21 includes the pixel circuit 10 between a substrate 51 and a substrate 59. The pixel circuit 10 includes a light-receiving element 13, the light-emitting element 11, and a layer 55 including a transistor. The light-emitting element 11 emits the infrared light 12, and the light-receiving element 13 senses the infrared light 14 entering the pixel array 21.

Each of the substrate 51 and the substrate 59 is preferably flexible. Accordingly, the flexibility of the imaging device 20 can be increased. Furthermore, an adhesive layer 57 is preferably provided on a surface side of the substrate 51, where the layer 55 including a transistor is not provided. For example, the adhesive layer 57 can be provided on a surface, of the substrate 51, which faces the surface provided with the layer 55. With the adhesive layer 57, the imaging device 20 can be fixed to an object, so that a highly convenient imaging device can be provided.

The layer 55 including a transistor preferably includes a first transistor and a second transistor. The first transistor is electrically connected to the light-receiving element 13. The second transistor is electrically connected to the light-emitting element 11.

In the layer 55 including a transistor, transistors, wirings electrically connected to the transistors, and the like are included. In the imaging device of one embodiment of the present invention, the light-receiving element 13 and the light-emitting element 11 are provided over the layer 55 including a transistor, whereby the infrared light 12 emitted from the light-emitting element 11 and the infrared light 14 entering the light-emitting element 13 can be prevented from being blocked by the wirings and the like, and imaging can be performed efficiently. Consequently, the imaging device can have low power consumption.

Figure 2C:
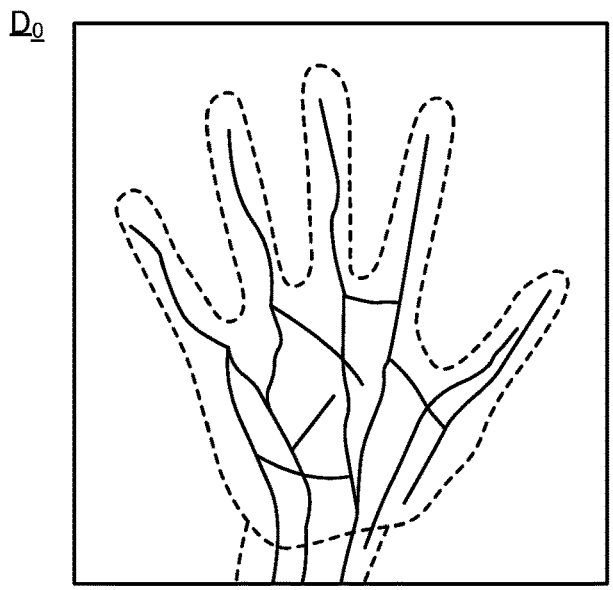
FIG. 2C shows an example of a vein image.

The imaging device of one embodiment of the present invention can be favorably used for an image capturing of a vein in the hand, for example. As illustrated in FIG. 2B, the infrared light 12 emitted from the light-emitting element 11 is scattered by the surface of the hand 52 and the biological tissue inside thereof, and part of the scattered light travels toward the light-receiving element 13 from the inside of the living body. This backscattering light 63 passes through a vein 61 and enters the light-receiving element 13. The vein 61 contains a large amount of hemoglobin not containing oxygen (also referred to as reduced hemoglobin) and hemoglobin containing oxygen (also referred to as oxyhemoglobin). Specifically, the reduced hemoglobin absorbs light whose wavelength is approximately 760 nm in the infrared light range. Thus, the amount of infrared light passing through the vein 61 is reduced, and a vein image $D_0$ can be captured. An example of the vein image $D_0$ is shown in FIG. 2C.

Although FIG. 2A and FIG. 2B each show an example in which the hand 52 of the imaging object is not in contact with the imaging device 20, the hand 52 may be in contact with the imaging device 20. For example, a spacer may be provided on a top surface of the imaging device 20 so that the imaging object is not in contact with the imaging device 20. A structure in which the imaging object is not in contact with the imaging device 20 inhibits the surface of the imaging device 20 from being contaminated, so that catching dirt in capturing an image can be inhibited. Alternatively, a structure in which the imaging object is in contact with the imaging device 20 inhibits entry of stray light into the imaging device 20 in capturing an image, so that catching the stray light in the captured image can be inhibited.

Figure 3A:
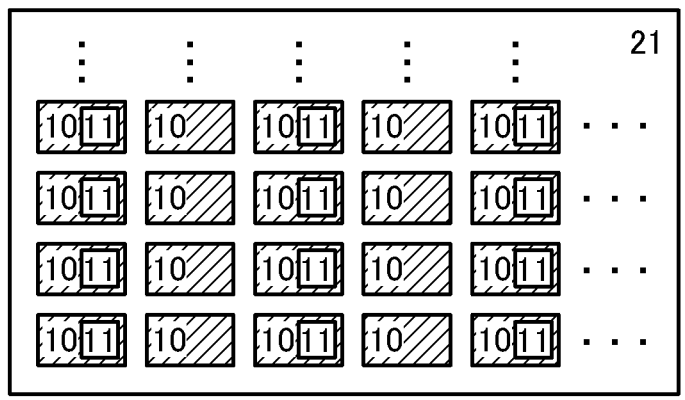
FIG. 3A, FIG. 3B, and FIG. 3C are diagrams each illustrating a pixel array.
Figure 3B:
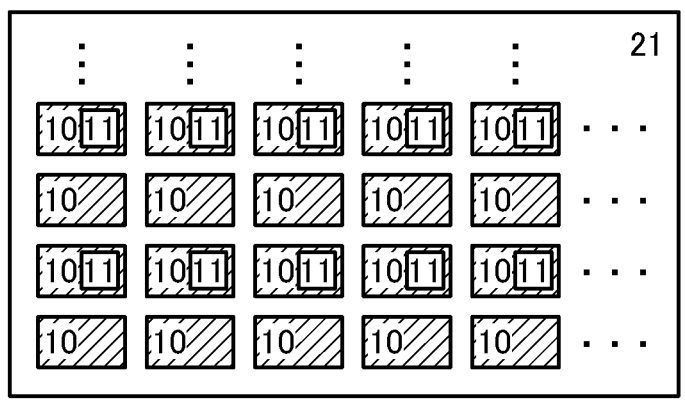
Figure 3C:
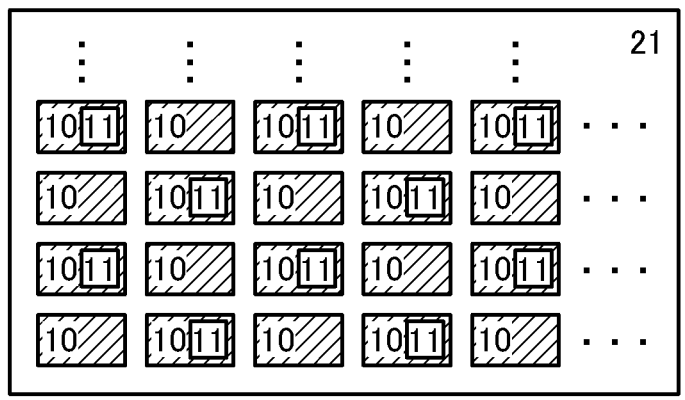

Note that in the case where the importance of resolution is not emphasized, a structure in which the pixel circuit 10 does not include the light-emitting element 11 may be employed. For example, as illustrated in FIG. 3A, the light-emitting element 11 may be positioned in every other column of the pixel circuit 10. Alternatively, the light-emitting element 11 may be arranged in every few columns of the pixel circuits 10. For example, as illustrated in FIG. 3B, the light-emitting element 11 may be positioned in every other row of the pixel circuit 10. Alternatively, the light-emitting element 11 may be arranged in every few rows of the pixel circuits 10. For example, the light-emitting element 11 may be arranged in a staggered manner as illustrated in FIG. 3C.

A circuit configuration of the pixel circuit that can be used for the imaging device of one embodiment of the present invention is described.

Figure 4A:
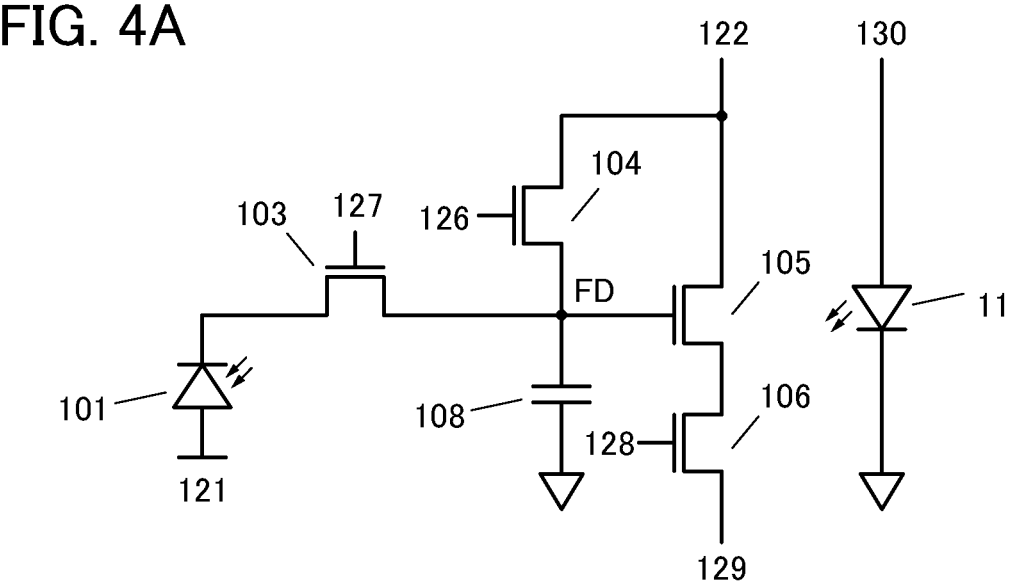
FIG. 4A, FIG. 4B, and FIG. 4C are diagrams each illustrating a pixel circuit.

FIG. 4A is a circuit diagram illustrating the pixel circuit 10 and the light-emitting element 11. The pixel circuit 10 can include a light-receiving element 101, a transistor 103, a transistor 104, a transistor 105, a transistor 106, and a capacitor 108. Note that a structure in which the capacitor 108 is not provided may be employed.

One electrode (cathode) of the light-receiving element 101 is electrically connected to one of a source and a drain of the transistor 103. The other of the source and the drain of the transistor 103 is electrically connected to one of a source and a drain of the transistor 104. The one of a source and a drain of the transistor 104 is electrically connected to one electrode of the capacitor 108. The one electrode of the capacitor 108 is electrically connected to a gate of the transistor 105. One of a source and a drain of the transistor 105 is electrically connected to one of a source and a drain of the transistor 106.

Here, a wiring that connects the other of the source and the drain of the transistor 103, the one electrode of the capacitor 108, and the gate of the transistor 105 is a node FD. The node FD can function as a charge accumulation portion.

The other electrode (anode) of the light-receiving element 101 is electrically connected to a wiring 121. A gate of the transistor 103 is electrically connected to a wiring 127. The other of the source and the drain of the transistor 104 and the other of the source and the drain of the transistor 105 are electrically connected to a wiring 122. A gate of the transistor 104 is electrically connected to a wiring 126. A gate of the transistor 106 is electrically connected to a wiring 128. The other electrode of the capacitor 108 is electrically connected to a reference potential line such as a GND wiring, for example. The other of the source and the drain of the transistor 106 is electrically connected to a wiring 129.

In FIG. 4A, one electrode of the light-emitting element 11 is electrically connected to a wiring 130. The other electrode of the light-emitting element 11 is electrically connected to a reference potential line such as a GND wiring, for example. Since the pixel circuit 10 and the light-emitting element 11 are not electrically connected in this structure, the input potential to the light-emitting element 11 and the timing of light emission can be controlled independently.

The wirings 127 and 128 can function as signal lines which control the electrical conduction of the respective transistors. The wiring 129 can function as an output line.

The wirings 121, 122, and 130 can have functions of power supply lines. The structure shown in FIG. 4A is a structure in which the cathode of the light-receiving element 101 is electrically connected to the transistor 103 and the node FD is reset to a high potential; accordingly, the wiring 122 is set to a high potential (a potential higher than that of the wiring 121). The wiring 130 has a function of supplying a potential for supplying a forward bias to the light-emitting element 11 and causing light emission.

Figure 4B:
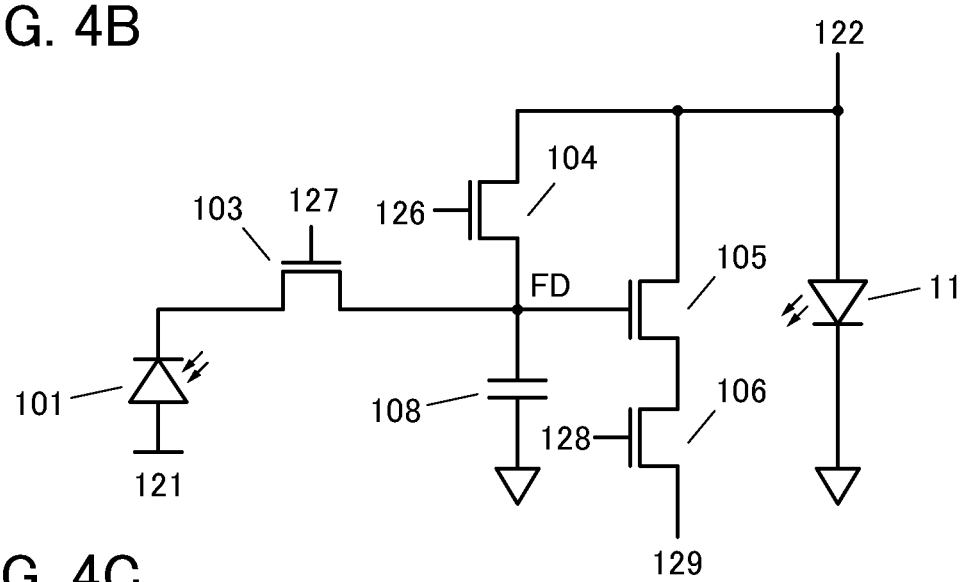

FIG. 4B illustrates a structure in which the one electrode of the light-emitting element 11 is electrically connected to the wiring 122. This structure can be employed in the case where a common potential can be used as the reset potential of the node FD, the power supply potential supplied to the transistor 105, and the input potential to the light-emitting element 11.

Figure 4C:
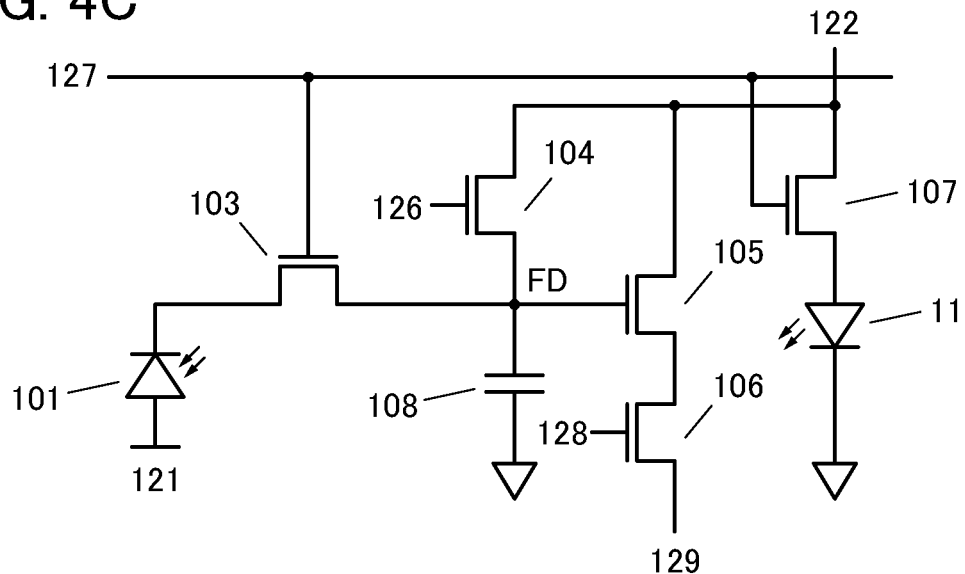

As illustrated in FIG. 4C, the transistor 107 may be added to the structure of FIG. 4B. One of a source and a drain of the transistor 107 is electrically connected to one electrode of the light-emitting element 11. The other of the source and the drain of the transistor 107 is electrically connected to the wiring 122. A gate of the transistor 107 is electrically connected to the wiring 127. With this structure, the light emission period can be limited to only a period during which the transistor 103 is on, whereby the power consumption can be reduced. Since the transistor 103 needs to be on only in a reset operation period and an accumulation operation period for the node FD, nonessential light emission in a reading operation period or the like can be suppressed.

Figure 5A:
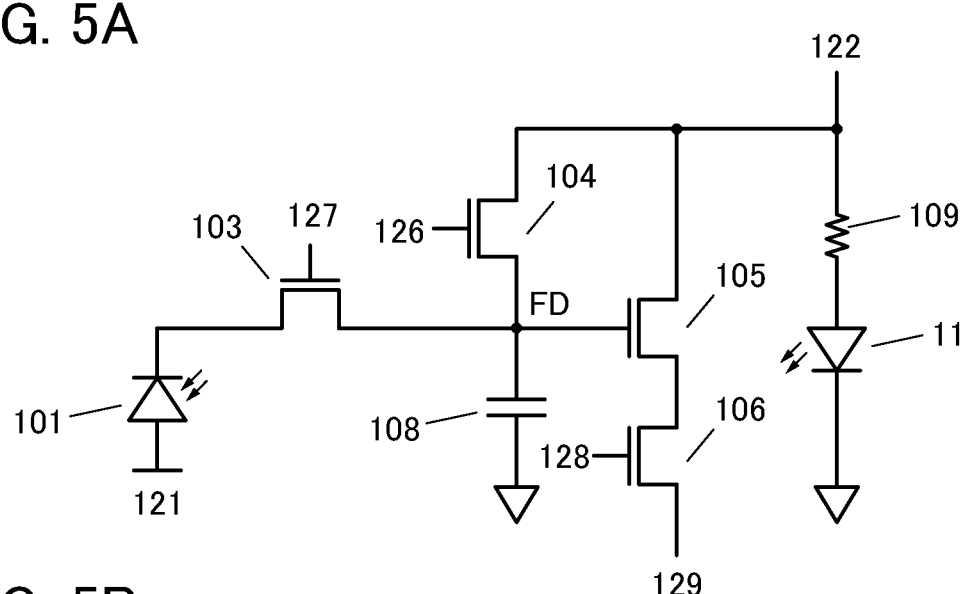
FIG. 5A, FIG. 5B, and FIG. 5C are diagrams each illustrating a pixel circuit.

Furthermore, in the case where the reset potential of the node FD or the like is too high compared with an appropriate potential input to the light-emitting element 11, a resistor 109 may be electrically connected between the one electrode of the light-emitting element 11 and the wiring 122 as illustrated in FIG. 5A. The resistor 109 operates as a current-limiting resistance; limiting the current flowing through the light-emitting element 11 can enhance the reliability of the light-emitting element 11. The resistance value of the resistor 109 may be selected so as to be suitable for electrical characteristics of the light-emitting element 11.

Figure 5B:
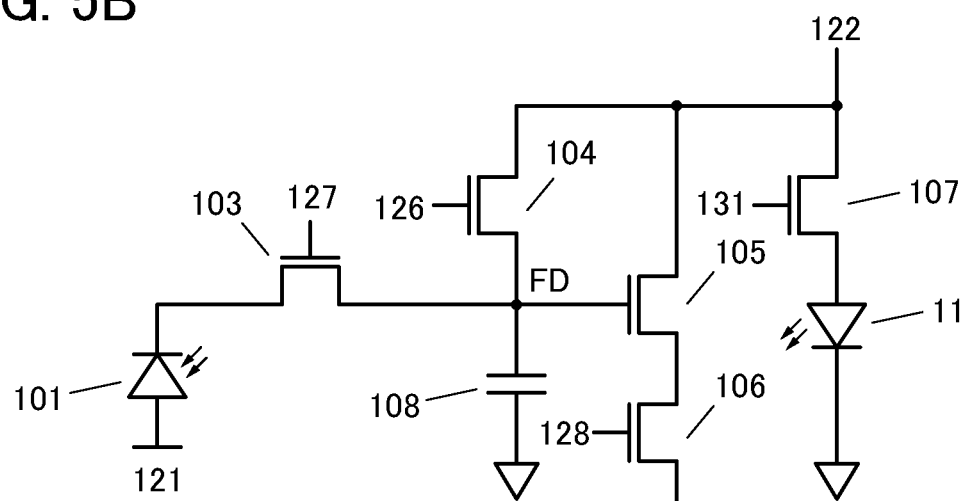

Note that as illustrated in FIG. 5B, the transistor 107 illustrated in FIG. 4C may operate as a substitute for the resistor 109. In this structure, the gate of the transistor 107 is electrically connected to a wiring 131. Thus, changing the potential of the wiring 131 allows appropriate control of the illuminance and the timing of light emission of the light-emitting element 11, so that power consumption can be suppressed.

Figure 5C:
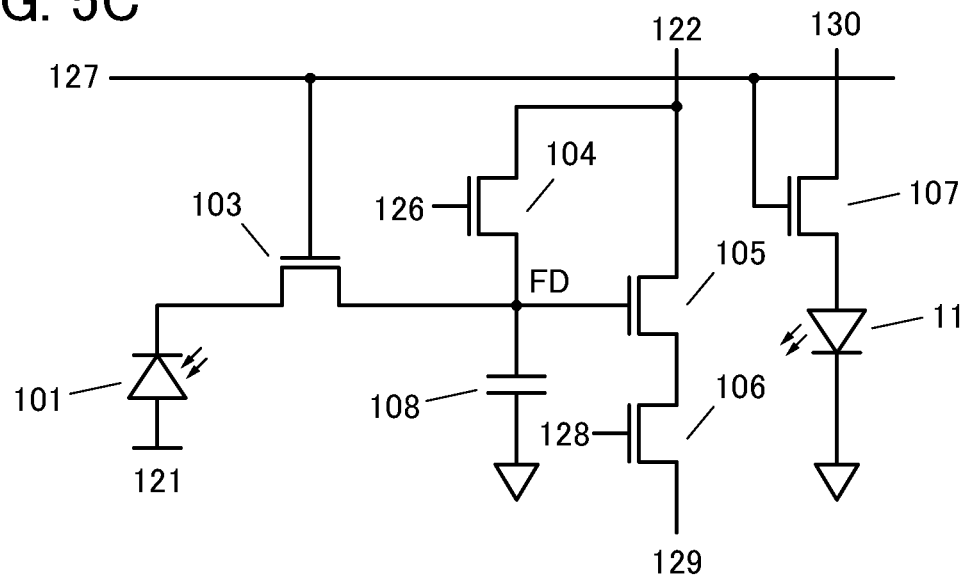
Figure 6A:
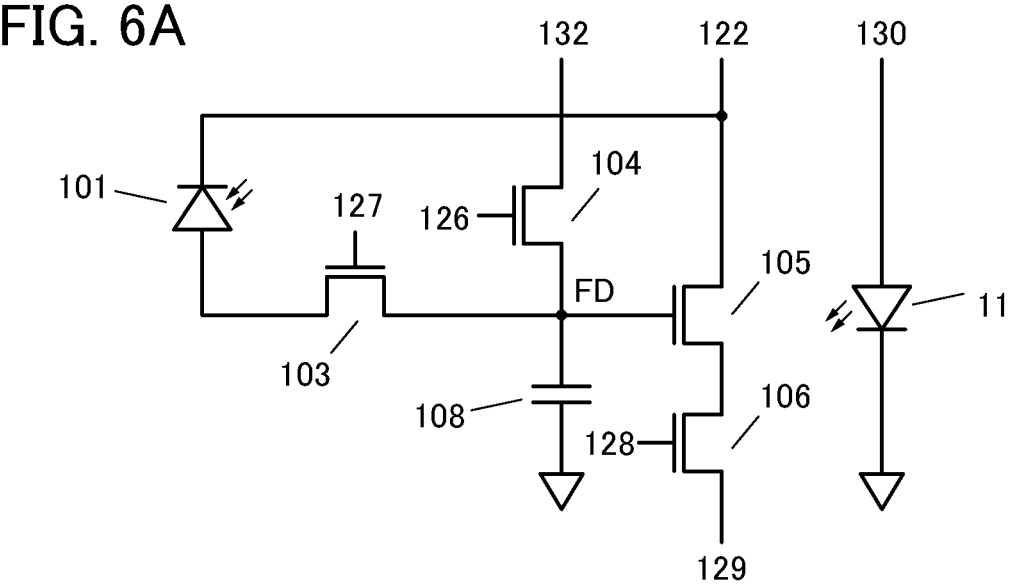
FIG. 6A, FIG. 6B, and FIG. 6C are diagrams each illustrating a pixel circuit.
Figure 6B:
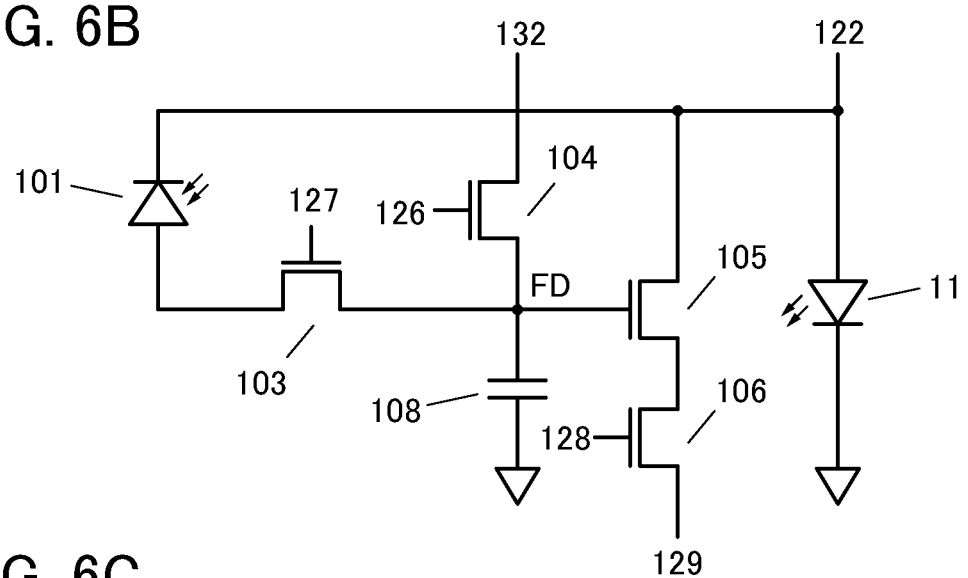
Figure 6C:
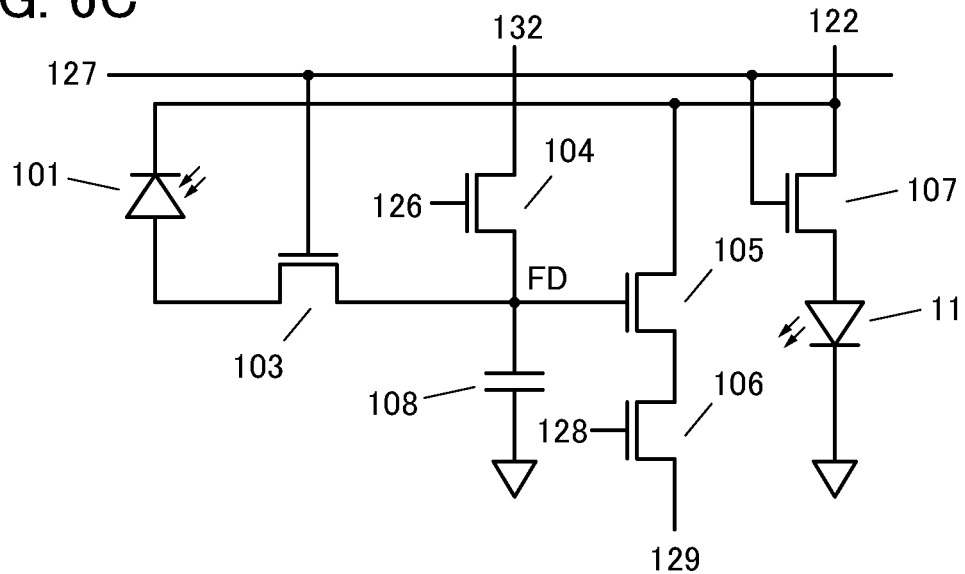
Figure 7A:
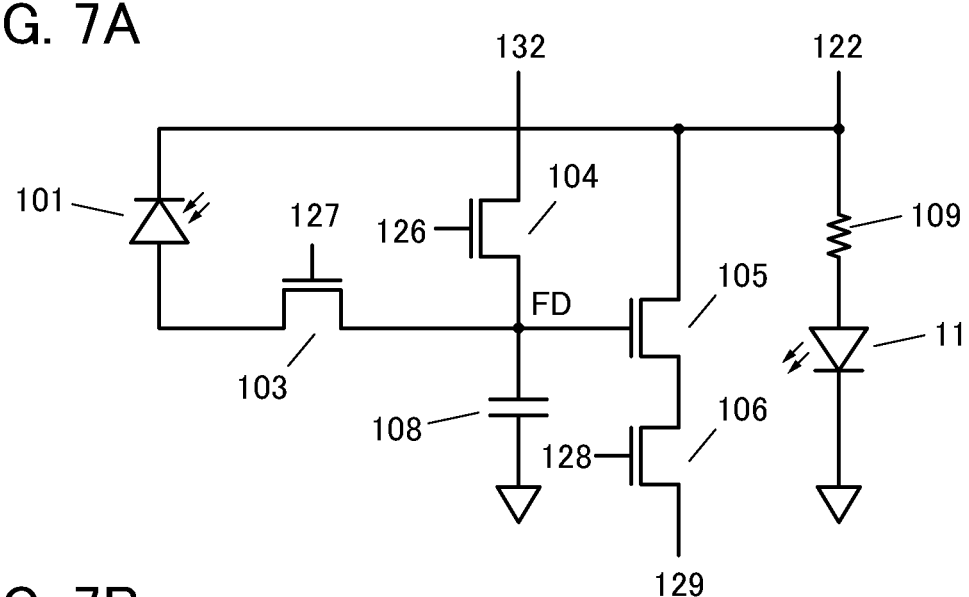
FIG. 7A, FIG. 7B, and FIG. 7C are views each illustrating a pixel circuit.
Figure 7B:
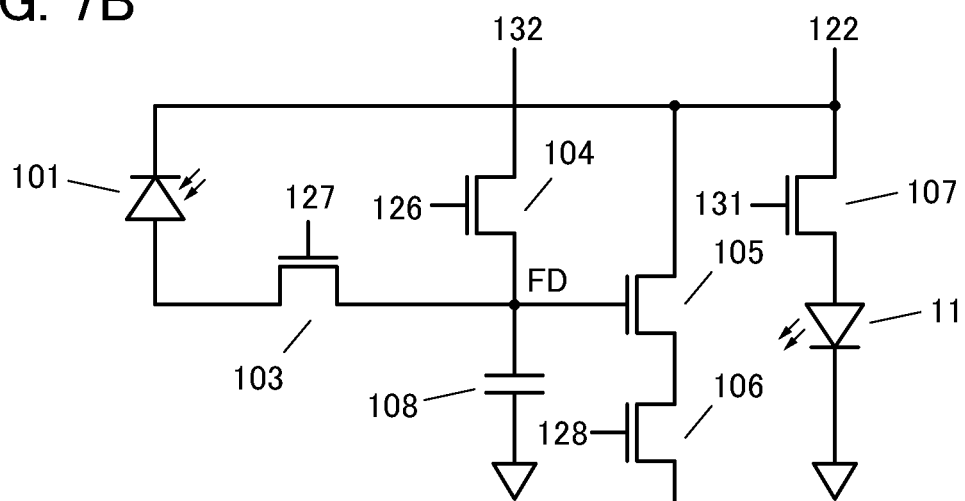
Figure 7C:
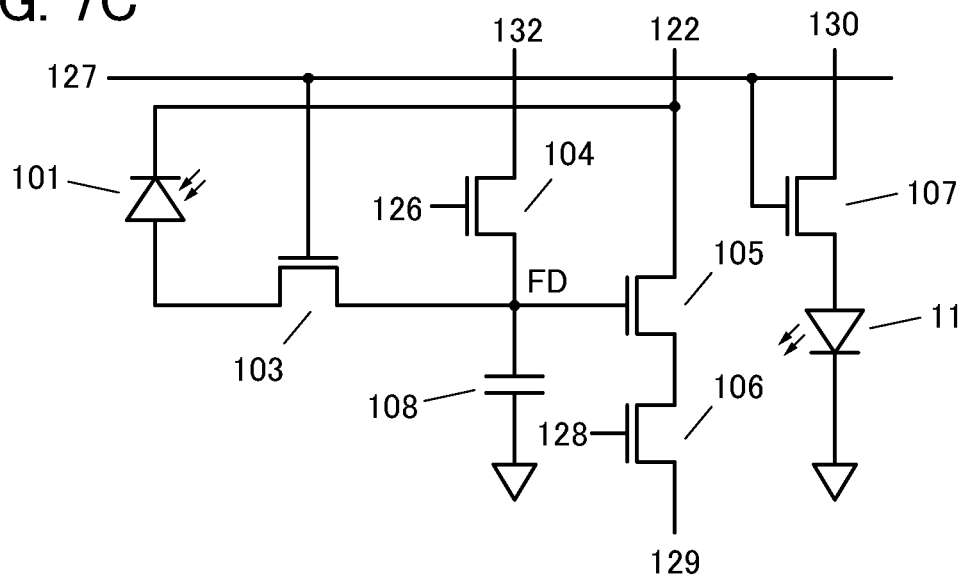

Furthermore, as illustrated in FIG. 5C, with the transistor 107 provided, the other of the source and the drain of the transistor 107 may be electrically connected to the wiring 130, and the gate of the transistor 107 may be electrically connected to the wiring 127. In this structure, the input potential to the light-emitting element 11 is controlled by the wiring 130, and the timing of light emission is controlled by the wiring 127.

Note that FIG. 4A to FIG. 4C and FIG. 5A to FIG. 5C show the structures in which the cathode of the light-receiving element 101 is electrically connected to the node FD. However, as illustrated in FIG. 6A to FIG. 6C and FIG. 7A to FIG. 7C, the anode of the light-receiving element 101 may be electrically connected to the node FD.

In the structures illustrated in FIG. 6A to FIG. 6C and FIG. 7A to FIG. 7C, the one electrode of the light-receiving element 101 is electrically connected to the wiring 122 and the other electrode of the light-receiving element 101 is electrically connected to the one of the source and the drain of the transistor 103. In addition, the other of the source and the drain of the transistor 104 is electrically connected to a wiring 132.

The wiring 132 can have a function of a power supply line or a supply line of a reset potential. The structures illustrated in FIG. 6A to FIG. 6C and FIG. 7A to FIG. 7C are structures in which the anode side of the light-receiving element 101 is electrically connected to the transistor 103 and the node FD is reset to a low potential in the operation; accordingly, the wiring 132 is set to a low potential (a potential lower than that of the wiring 122).

For the connection between the light-emitting element 11 and the peripheral components illustrated in FIG. 6A to FIG. 6C and FIG. 7A to FIG. 7C, the descriptions for FIG. 4A to FIG. 4C and FIG. 5A to FIG. 5C can be referred to.

As the light-receiving element 101, a photodiode can be used. In one embodiment of the present invention, imaging using infrared light is performed. Accordingly, a photodiode that can photoelectrically convert infrared light is used as the light-receiving element 101. For example, a pn-junction photodiode using single crystal silicon for a photoelectric conversion portion, a pin photodiode using polycrystalline silicon or microcrystalline silicon for a photoelectric conversion layer, or the like can be used. Alternatively, a material that can photoelectrically convert infrared light, such as a compound semiconductor, may be used.

In one embodiment of the present invention, an organic photodiode including a layer containing an organic compound can be favorably used as the light-receiving element 101. The organic photodiode, which is easily made thin, lightweight, and large in area and has a high degree of freedom for shape and design, can be used in a variety of imaging devices.

The transistor 103 has a function of controlling the potential of the node FD. The transistor 104 has a function of resetting the potential of the node FD. The transistor 105 functions as a source follower circuit, and can output the potential of the node FD as image data to the wiring 129. The transistor 106 has a function of selecting a pixel from which the image data is output.

Transistors using a metal oxide in their channel formation regions (hereinafter, OS transistors) are preferably used as the transistor 103 and the transistor 104. The OS transistor has a feature of extremely low off-state current. When OS transistors are used as the transistors 103 and 104, the charge-retention period at the node FD can be prolonged greatly. Therefore, a global shutter mode in which charge accumulation operation is performed in all the pixels at the same time can be used without complicating the circuit structure and operation method. An imaging device with high reliability can be provided.

FIG. 8A is a schematic view of the operation method with the rolling shutter mode, and FIG. 8B is a schematic view of the operation method with the global shutter mode. Note that En denotes exposure (accumulation operation) in the n-th column (n is a natural number), and Rn denotes reading operation in the n-th column. FIG. 8A and FIG. 8B show operation from the first row to the M-th row (M is a natural number).

The rolling shutter mode is for an operation method in which the exposure and data reading are performed sequentially and a reading period of a row overlaps with an exposure period of another row. The reading operation is performed right after the exposure, so that imaging can be performed even with a circuit structure having a relatively short data holding period. However, an image of one frame is composed of data that does not have simultaneity of imaging; therefore, distortion is caused in an image when imaging of a moving object is performed.

On the other hand, the global shutter mode is for an operation method in which exposure is performed on all the pixels simultaneously, data is held in each pixel, and data reading is performed row by row. Thus, an image without distortion can be obtained even when an image of a moving object is captured.

In the case where a transistor having a relatively high off-state current, such as a transistor that uses Si in its channel formation region (hereinafter, Si transistor), is used in a pixel circuit, a data potential is likely to outflow from a charge accumulation portion; therefore, a rolling shutter method is used. In order to achieve the global shutter mode using a Si transistor, a memory circuit or the like needs to be provided additionally, and more complex operation has to be performed at high speed. On the other hand, when an OS transistor is used in a pixel circuit, the data potential hardly leaks from the charge-accumulated portion, which easily enables the global shutter mode.

OS transistors may also be used as the transistors 105 and 106. Furthermore, all the transistors included in the imaging device of one embodiment of the present invention may be either OS transistors or Si transistors. When one kind of transistors, such as an OS transistor, is adopted for all of the transistors in the imaging device, the manufacturing process of the imaging device can be simplified. Thus, the manufacturing cost of the imaging device can be reduced. Note that an OS transistor and a Si transistor may be freely used in combination. Examples of the Si transistor include a transistor containing amorphous silicon and a transistor containing crystalline silicon (typically, low-temperature polysilicon, single crystal silicon, or the like).

As the light-emitting element 11, an EL element such as an OLED (Organic Light Emitting Diode) or a QLED (Quantum-dot Light Emitting Diode) is preferably used. As the light-emitting substance contained in the EL element, a substance emitting fluorescence (a fluorescent material), a substance emitting phosphorescence (a phosphorescent material), an inorganic compound (e.g., a quantum dot material), a substance exhibiting thermally activated delayed fluorescence (a thermally activated delayed fluorescent (TADF) material), or the like can be given. Alternatively, a light-emitting diode (LED) such as a micro-LED can be used as the light-emitting element.

In one embodiment of the present invention, an EL element can be favorably used as the light-emitting element 11. As the EL element, an element emitting infrared light can be used. In particular, the EL element preferably emits near-infrared light having a peak at a wavelength greater than or equal to 700 nm and less than or equal to 2500 nm. For example, light having a wavelength of 760 nm and its vicinity is likely to be absorbed by reduced hemoglobin in a vein, so that the position of the vein can be detected by making an image from received reflected light from a palm, a finger, or the like. This action can be utilized for biometric authentication. In addition, it can be used for a nondestructive inspection such as inspection of a foreign matter in food or failure analysis of industrial products by using near-infrared light having an appropriate wavelength. Furthermore, when combined with the global shutter mode, highly accurate sensing becomes possible even while an object is moving.

When an EL element is used as the light-emitting element 11, a thin imaging device with a light source can be achieved. The imaging device can easily be incorporated in various devices and the portability can be improved.

In one embodiment of the present invention, organic EL elements are used as the light-emitting elements, and organic photodiodes are used as the light-receiving elements. A large number of layers of the organic photodiode can be shared with the organic EL element. Accordingly, the light-receiving element can be incorporated into the imaging device without a significant increase in the number of manufacturing steps. For example, an active layer of the light-receiving element and a light-emitting layer of the light-emitting element are separately formed, and the other layers can be shared by the light-emitting element and the light-receiving element.

Figure 9A:
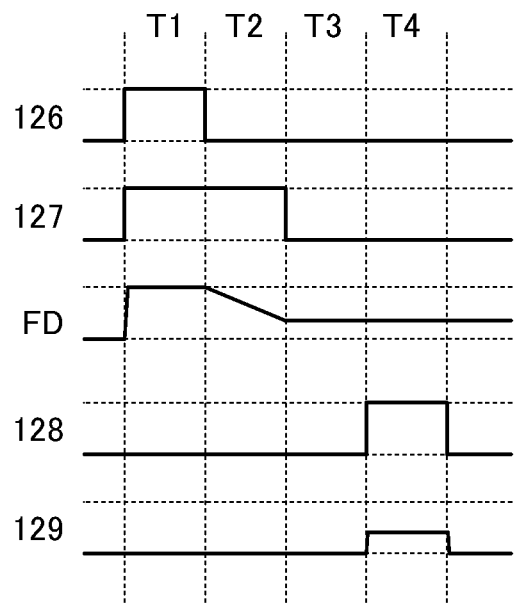
FIG. 9A and FIG. 9B are timing charts illustrating operations of a pixel circuit.

Next, an example of the operation of the pixel circuits 10 illustrated in FIG. 4A to FIG. 4C and FIG. 5A to FIG. 5C is described with reference to a timing chart of FIG. 9A. Note that in the description of the timing chart in this specification, a high potential is denoted by "H" and a low potential is denoted by "L". The wiring 121 is always supplied with "L", and the wiring 122 is always supplied with "H".

Note that the light-emitting element 11 is in a state of being supplied with a power supply potential for appropriately causing light emission at least in an accumulation operation period.

In a period T1, the potential of the wiring 126 is set to "H", the potential of the wiring 127 is set to "H", and the potential of the wiring 128 is set to "L", whereby the transistors 103 and 104 are turned on and the potential "H" of the wiring 122 is supplied to the node FD (reset operation).

In a period T2, the potential of the wiring 126 is set to "L", the potential of the wiring 127 is held at "H", and the potential of the wiring 128 is held at "L", whereby the transistor 104 is turned off, and supply of the reset potential is stopped. Furthermore, the potential of the node FD is decreased in accordance with the operation of the light-receiving element 101 (accumulation operation).

In a period T3, the potential of the wiring 126 is held at "L", the potential of the wiring 127 is set to "L", and the potential of the wiring 128 is held at "L", whereby the transistor 103 is turned off, and the potential of the node FD is fixed and held (holding operation). At this time, OS transistors, whose off-state current is low, are used as the transistor 103 and the transistor 104, which are connected to the node FD, whereby unnecessary charge leakage from the node FD can be suppressed and the data-retention time can be extended.

In a period T4, the potential of the wiring 126 is held at "L", the potential of the wiring 127 is held at "L", and the potential of the wiring 128 is set to "H", whereby the transistor 106 is turned on, and the potential of the node FD is read out to the wiring 129 by source follower operation of the transistor 105 (reading operation).

The above is the example of the operation of the pixel circuits 10 illustrated in FIG. 4A to FIG. 4C and FIG. 5A to FIG. 5C.

Figure 9B:
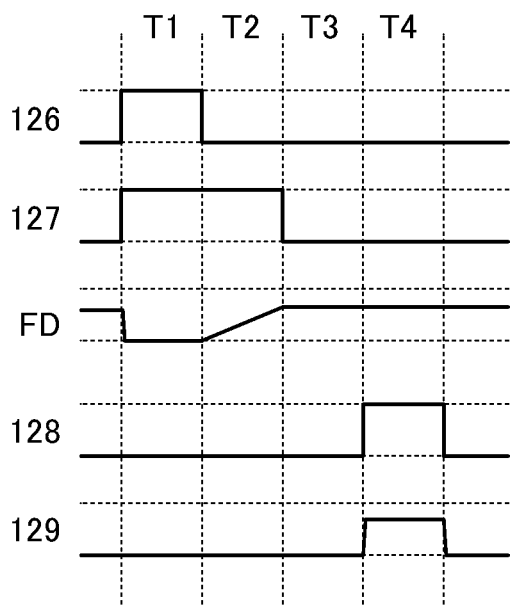

The pixel circuits 10 illustrated in FIG. 6A to FIG. 6C and FIG. 7A to FIG. 7C can be operated in accordance with the timing chart of FIG. 9B. Note that the wiring 122 is always supplied with "H", and the wiring 132 is always supplied with "L". The fundamental operation is similar to that described above with the timing chart of FIG. 9A.

Figure 10A:
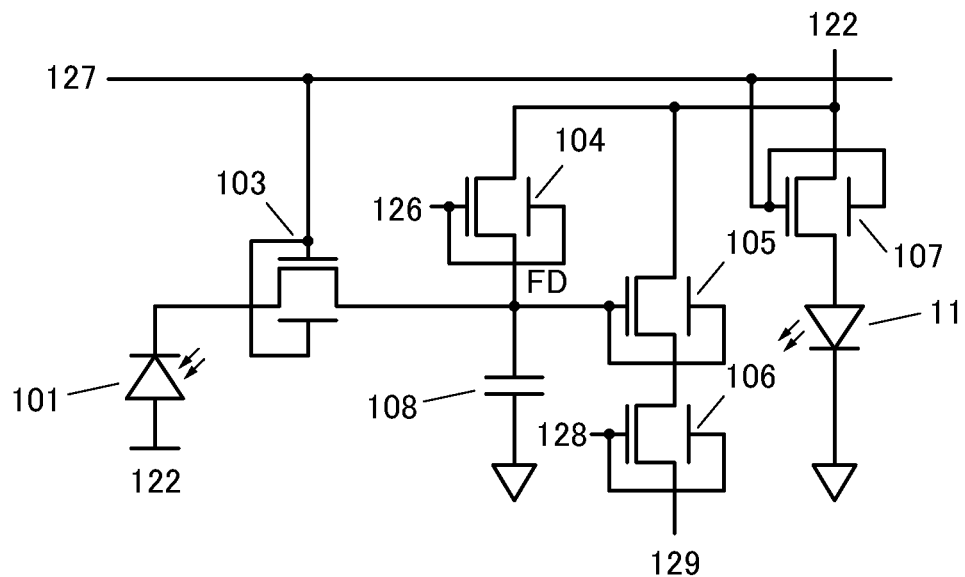
FIG. 10A and FIG. 10B are diagrams each illustrating a pixel circuit.
Figure 10B:
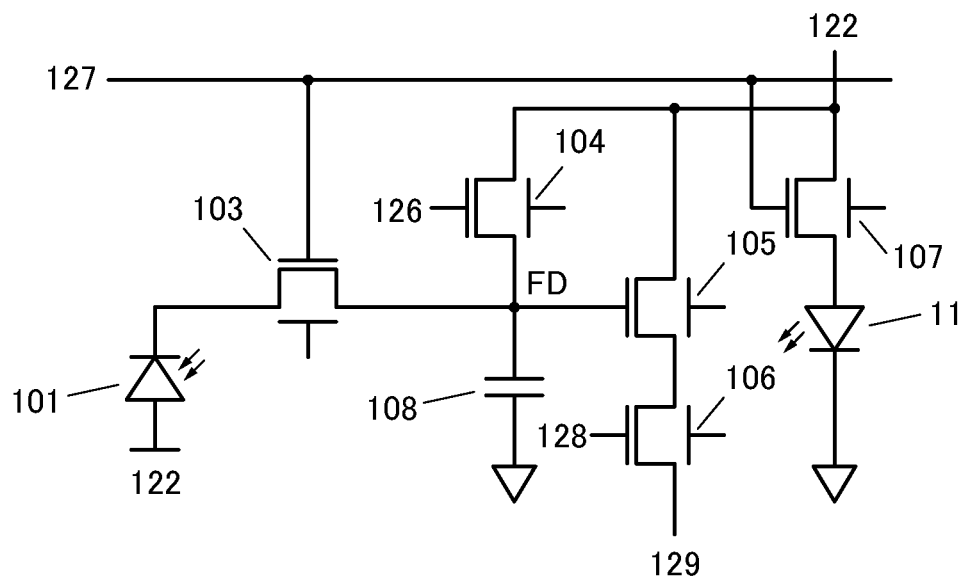

In one embodiment of the present invention, as shown in examples of FIG. 10A and FIG. 10B, a structure in which transistors are provided with back gates may be employed. FIG. 10A shows a structure in which back gates are electrically connected to front gates, which brings an effect of increasing on-state currents. FIG. 10B shows a structure in which the back gates are electrically connected to wirings capable of supplying a constant potential, which enables the threshold voltage of the transistors to be controlled.

In addition, a structure which enables each transistor to perform appropriate operation, for example, a structure obtained by combination of FIG. 10A and FIG. 10B, may be employed. The pixel circuit may include a transistor not provided with a back gate. Note that the structure of a transistor provided with a backgate can be employed for all the structures illustrated in FIG. 4A to FIG. 4C, FIG. 5A to FIG. 5C, FIG. 6A to FIG. 6C, and FIG. 7A to FIG. 7C.

At least part of the structure examples, the drawings corresponding thereto, and the like exemplified in this embodiment can be implemented in combination with the other structure examples, the other drawings, and the like as appropriate.

At least part of this embodiment can be implemented in combination with the other embodiments described in this specification as appropriate.

Embodiment 2

In this embodiment, an authentication device of one embodiment of the present invention will be described with reference to FIG. 11 to FIG. 14.

Figure 11A:
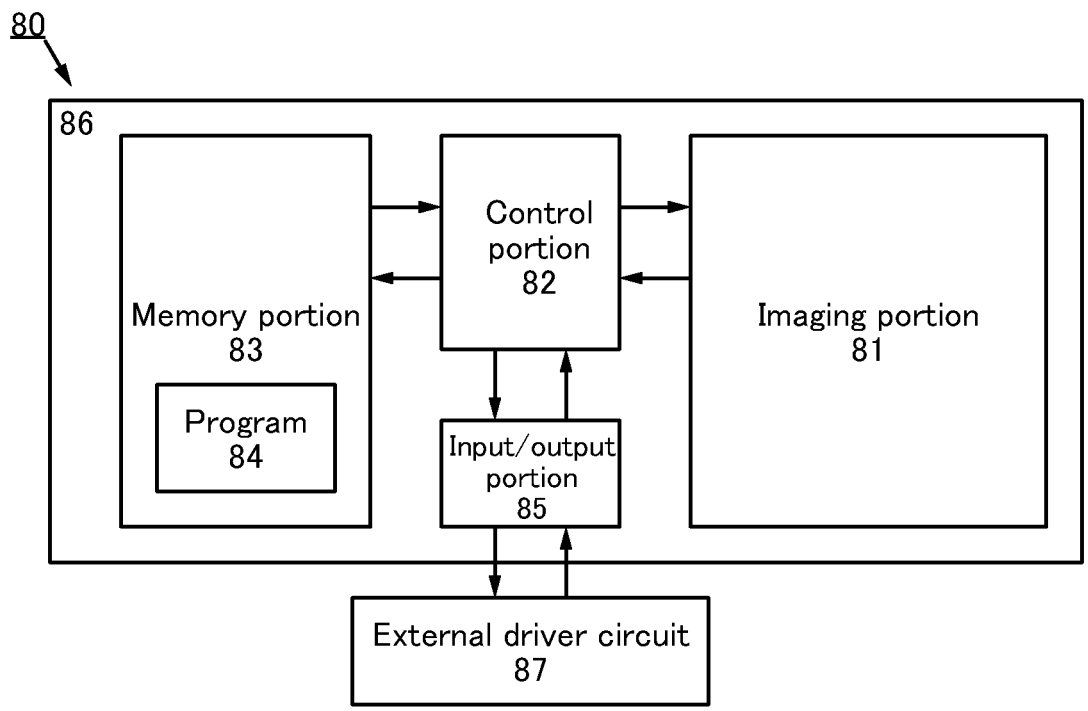
FIG. 11A is a block diagram illustrating an authentication device.

FIG. 11A is a block diagram of an authentication device 80. In the authentication device 80, an authentication portion 86 at least includes an imaging portion 81, a control portion 82, a memory portion 83, and an input/output portion 85. A program 84 is stored in the memory portion 83. The authentication device 80 may further include an external driver circuit 87.

Figure 11B:
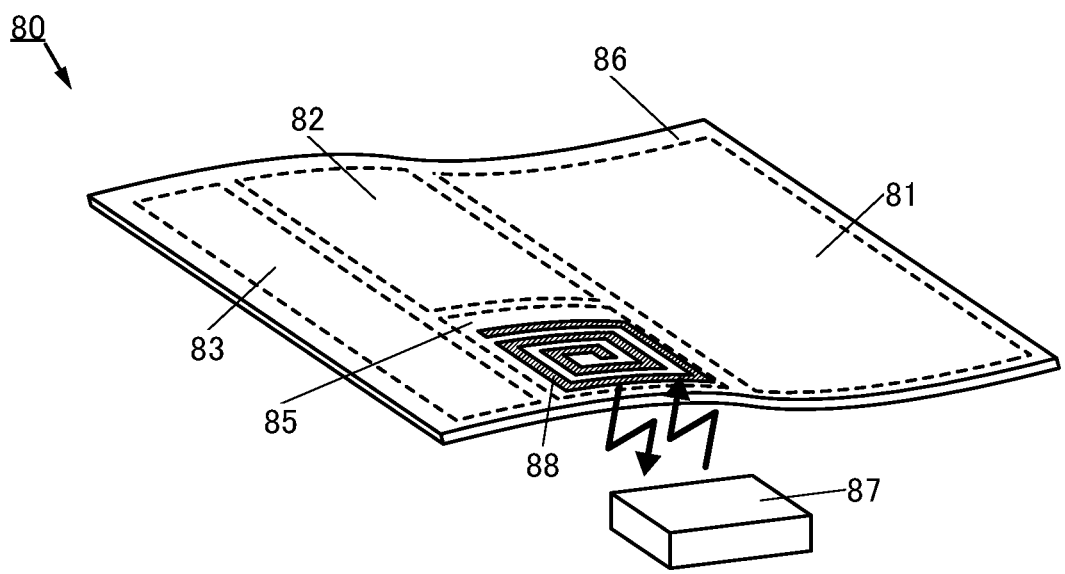
FIG. 11B is a perspective view of the authentication device.

An example of an external view of the authentication device 80 is shown. FIG. 11B is a perspective view of the authentication device 80. The authentication portion 86 has a sheet-like shape and further has flexibility as illustrated in FIG. 11B. The authentication portion 86 having flexibility can be provided on an object having a curved surface, such as a door knob or a steering wheel of an automobile. In addition, the authentication portion 86 includes an adhesive layer (not illustrated) on its surface. With the adhesive layer, the authentication portion 86 can be fixed to the object, so that the authentication device 80 can become a highly convenient device. For example, an adhesive layer can be provided on a surface of the authentication portion 86, which faces the surface provided with the imaging portion 81.

The imaging portion 81 has a function of capturing an image. In the imaging portion 81, a semiconductor device in which light-emitting elements and light-receiving elements are arranged in a matrix can be used. In the imaging portion 81, light-emitting elements emitting infrared light and light-receiving elements sensing infrared light are preferably used. For example, the above-described imaging device 20 can be favorably used as the imaging portion 81.

The memory portion 83 has a function of storing at least the program 84. In accordance with a request from the control portion 82, the memory portion 83 can output stored data to the control portion 82 or store the data. The program 84 stored in the memory portion 83 is read out and then executed by the control portion 82.

As the memory portion 83, a memory device using a nonvolatile memory element, such as a flash memory, an MRAM (Magnetoresistive Random Access Memory), a PRAM (Phase change RAM), an ReRAM (Resistive RAM), or an FeRAM (Ferroelectric RAM); a memory device using a volatile memory element, such as a DRAM (Dynamic RAM) or an SRAM (Static RAM); or the like may be used, for example. Furthermore, a memory media drive such as a hard disk drive (HDD) or a solid state drive (SSD) may be used, for example.

Note that the memory portion 83 is preferably formed using an OS transistor. Since the OS transistor has an extremely low off-state current, the OS transistor is used as a switch for retaining electric charge (data) flowing into a capacitor functioning as a memory element, whereby a long data retention period can be ensured. Accordingly, a highly reliable authentication device can be provided.

A memory device that can be connected and disconnected through an external interface with a connector, such as an HDD or an SSD, or a media drive for a recording medium such as a flash memory, a Blu-ray disc (registered trademark), or a DVD can also be used as the memory portion 83. Note that the memory portion 83 is not incorporated in the authentication device 80, and a memory device located outside thereof may be used as the memory portion 83. In that case, the memory portion 83 may be connected through the external interface or have a structure in which data transmission and reception may be wirelessly performed using a communication module.

The program 84 may be stored in an external server. In this case, when a user accesses the server, part or all of the program 84 may be stored in the memory portion 83 temporarily, permanently, or semipermanently (the case where an available period or an available number of times is set), and may be executed by the control portion 82.

The control portion 82 has a function of collectively controlling the components such as the imaging portion 81, the memory portion 83, and the input/output portion 85.

The control portion 82 interprets and executes instructions from various programs with use of a processor to process various kinds of data and control programs. A program that can be executed by the processor is read out from the memory portion 83, stored in a memory region of the processor temporarily, and executed.

A transistor including a metal oxide in its channel formation region (hereinafter an OS transistor) is preferably used in the control portion 82. With use of the OS transistor for a register or a cache memory in the control portion 82, the control portion 82 is made to operate only when necessary and otherwise made to store information on the previous processing in the memory element, whereby the authentication device 80 can have low power consumption.

A central processing unit (CPU) and other microprocessors such as a DSP (Digital Signal Processor) and a GPU (Graphics Processing Unit) can be used alone or in combination as the control portion 82. A structure may be employed in which such a microprocessor is obtained with a PLD (Programmable Logic Device) such as an FPGA (Field Programmable Gate Array) or an FPAA (Field Programmable Analog Array).

The input/output portion 85 has a function of inputting and outputting data to the outside. The input/output portion 85 includes an antenna 88, and a wireless signal is received and transmitted from/to the external driver circuit 87 by the antenna 88. For example, with the input/output portion 85, the authentication device 80 and an external device can be connected to each other through a cable. Alternatively, the input/output portion 85 may include a LAN (Local Area Network) connection terminal, an AC adaptor connection terminal, or the like. Without limitation to wire communication, a transceiver for optical communication using infrared rays, visible light, ultraviolet rays, or the like may be provided as the input/output portion 85.

The input/output portion 85 may have a structure supplied with power wirelessly by the antenna 88. Note that the shape and number of windings of the antenna 88 illustrated in FIG. 11B are just examples, and one embodiment of the present invention is not limited thereto. For example, other than the coil shape illustrated in FIG. 11B, a linear shape or a flat-plate shape may be employed.

The external driver circuit 87 transmits a signal to a managed object to be activated only when a user is authenticated by the authentication device 80, so that the managed object can be activated. For example, in the case where the managed object is a door having an electronic lock, the external driver circuit 87 transmits a signal for unlocking to the door, whereby the door can be opened. For example, in the case where the managed object is an automobile, the external driver circuit 87 transmits a signal for unlocking a door to the automobile, so that the door can be opened. For example, in the case where a managed object is an automobile or a motor-assisted bicycle, a signal for starting an engine is transmitted to the automobile or the motor-assisted bicycle, so that the engine for the automobile or the motor-assisted bicycle can be started.

As the external driver circuit 87, besides a CPU, other microprocessors such as DSP and GPU can be used alone or in combination. Furthermore, such a microprocessor may be achieved by a PLD such as an FPGA or a FPAA.

All the transistors included in the authentication device of one embodiment of the present invention may be either OS transistors or Si transistors. When one kind of transistors, such as an OS transistor, is adopted for all of the transistors in the authentication device, the manufacturing process of the authentication device can be simplified. Thus, the manufacturing cost of the authentication device can be reduced. Note that an OS transistor and a Si transistor may be freely used in combination.

Figure 12:
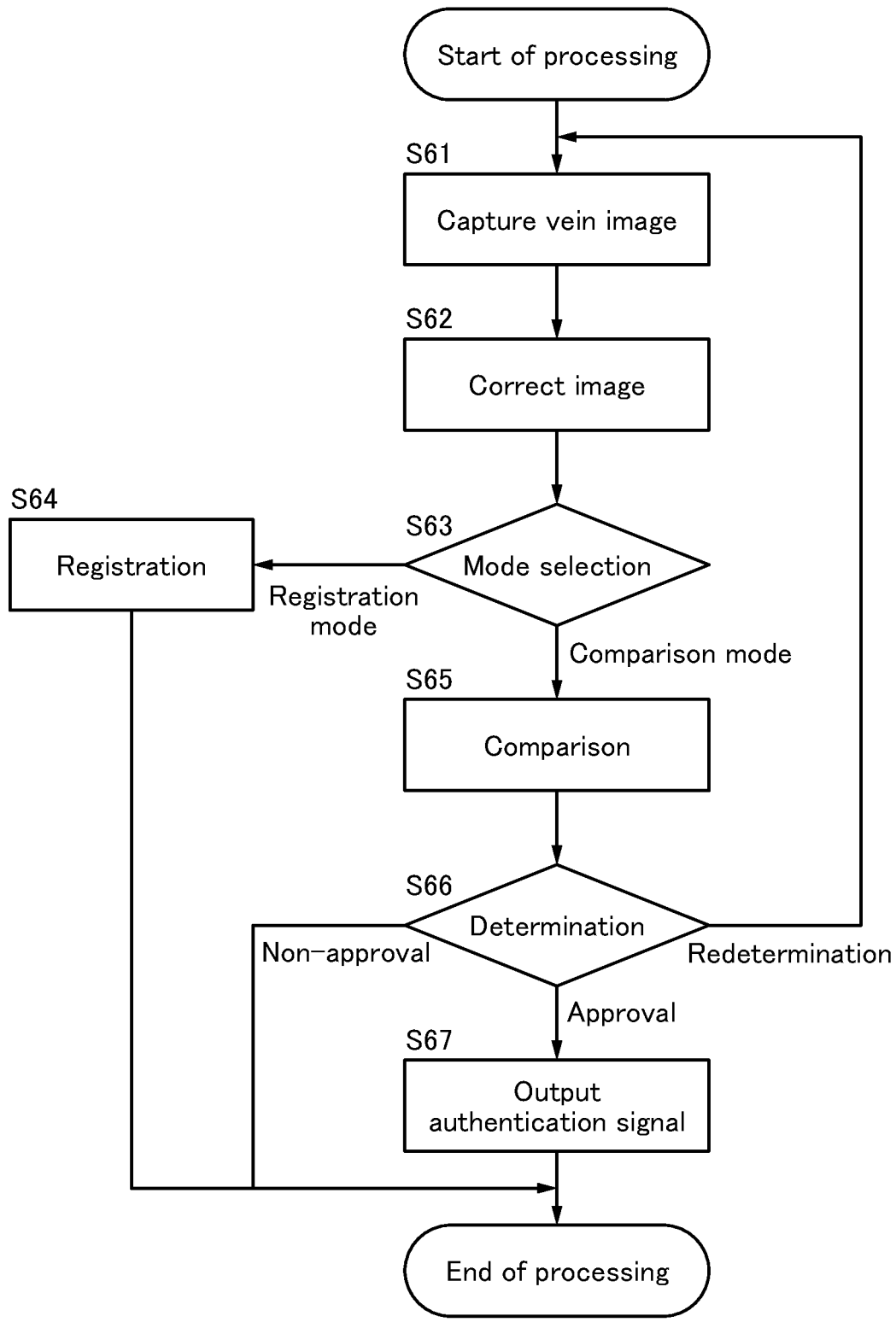
FIG. 12 is a flow chart showing an operation of an authentication device.

Next, an operation example of the authentication device 80 is described with reference to a flow chart in FIG. 12. FIG. 12 shows an example in which an image of a vein is captured and authentication is performed with the vein image. In addition, FIG. 12 exemplifies pattern matching where a pattern of the vein image is compared for determination; however, one embodiment of the present invention is not limited thereto. A minutia method utilizing minutiae such as ridge endings and bifurcations of the pattern in the vein image may be used.

First, in step S61, the control portion 82 requires the imaging portion 81 to perform imaging operation, and accordingly the imaging portion 81 performs imaging and outputs the captured vein image $D_0$ to the control portion 82 (that is, the control portion 82 reads out the vein image $D_0$ from the imaging portion 81). The control portion 82 may make the vein image $D_0$ to be stored in the memory portion 83 or held in the control portion 82.

Next, in Step S62, the control portion 82 reads out the program 84 from the memory portion 83 and executes the program to correct the vein image Do, thereby generating a new vein image $D_1$. As the correction, the position of the object in the image, unevenness of the image caused by noise or stray light in image capturing, or the like is corrected. In the case of using a minutia method, feature points of the vein image $D_1$ are extracted.

Next, in Step S63, the mode selection is performed to select a registration mode or a comparison mode. When a vein image of a user is registered in the authentication device 80, the registration mode is selected. When comparison with the vein image of the user that has been already registered in the authentication device 80 is performed, the comparison mode is selected.

In the case of the registration mode, in Step S64, the control portion 82 stores the vein image $D_1$ in the memory portion 83. Hereinafter, the vein image $D_1$ stored in the memory portion 83 is referred to as a registered image $D_T$. Alternatively, the control portion 82 may output the vein image $D_1$ to the input/output portion 85. In the case of using a minutia method, the feature points are stored in the memory portion 83. Alternatively, the feature points may be output to the input/output portion 85.

In the case of the comparison mode, in Step S65, the control portion 82 reads out the registered image $D_T$ of the user from the memory portion 83 to the control portion 82 and compares the vein image $D_1$ generated in Step S62. In the cases where registered images $D_T$ of a plurality of users exist, the vein image $D_1$ may be compared with each of the registered images $D_T$. In the case of using the minutia method, the control portion 82 checks the feature points.

Next, determination is performed in Step S66. When the registered image $D_T$ and the vein image $D_1$ match each other, authentication is approved. When the registered image $D_T$ and the vein image $D_1$ do not match each other, authentication is not approved. When authentication is not approved, the processing may be terminated after the determination. In the case where whether the registered image $D_T$ and the vein image $D_1$ match each other is not clearly determined, determination is performed again. When determination is performed again, the processing may return to Step S61 to capture a vein image again.

When authentication is approved, in Step S67, the control portion 82 outputs a signal of authentication to the input/output portion 85, and in accordance with it, the input/output portion 85 transmits a signal of authentication to the external driver circuit 87.

The program 84 includes a program for executing the above-described image processing and comparison in the control portion 82.

Next, a method for unlocking a door with use of the authentication device 80 is described.

Figure 13A:
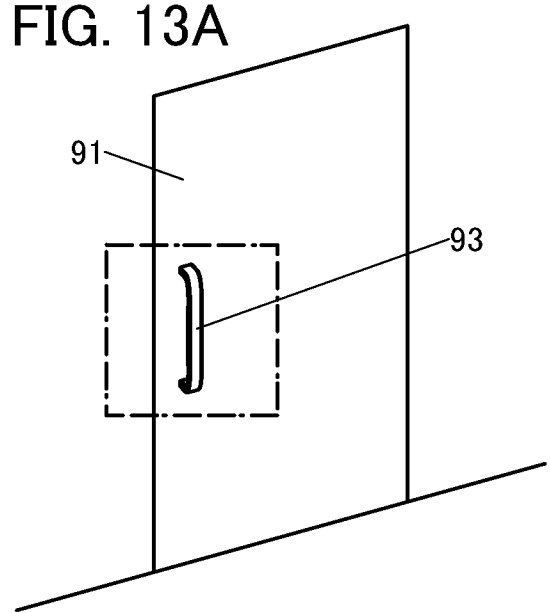
FIGS. 13A and FIG. 13B are diagrams illustrating an example of a door.
Figure 13B:
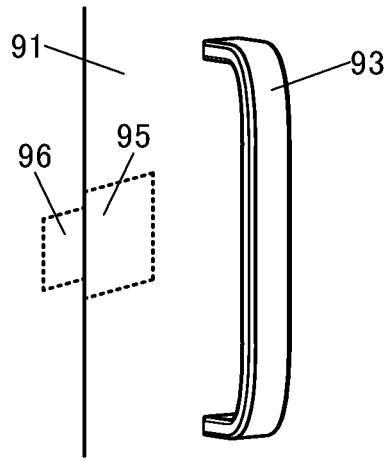

FIG. 13A shows an example of a door installed in a building, and FIG. 13B shows an enlarged view of a region surrounded by a dashed line in FIG. 13A. A door 91 illustrated in FIG. 13A and FIG. 13B includes a door knob 93 and an electronic lock 95. The electronic lock 95 has a function of electrically activating a bolt (dead bolt) 96 to unlock and lock the door.

Figure 13C:
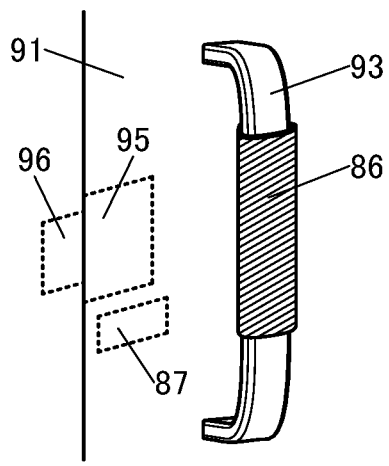
FIG. 13C, FIG. 13D, and FIG. 13E are perspective views illustrating an example of an authentication device.

FIG. 13C shows an example in which the authentication portion 86 of the authentication device of one embodiment of the present invention is installed on the door knob 93. The authentication portion 86 has flexibility and includes the adhesive layer 57 on its surface, whereby the authentication portion 86 can be easily installed on the door knob 93. The authentication portion 86 is preferably installed in a wide range on the door knob 93. When the authentication portion 86 is installed in a wide range on the door knob 93, a contact area of the authentication portion 86 with a hand of a user is large, which enhances the accuracy of authentication.

The external driver circuit 87 is connected to the electronic lock 95 through a signal cable (not illustrated), and a signal is transmitted from the external driver circuit 87 to the electronic lock 95.

Figure 13D:
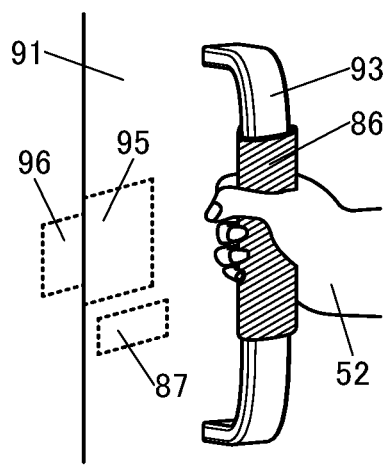
Figure 13E:
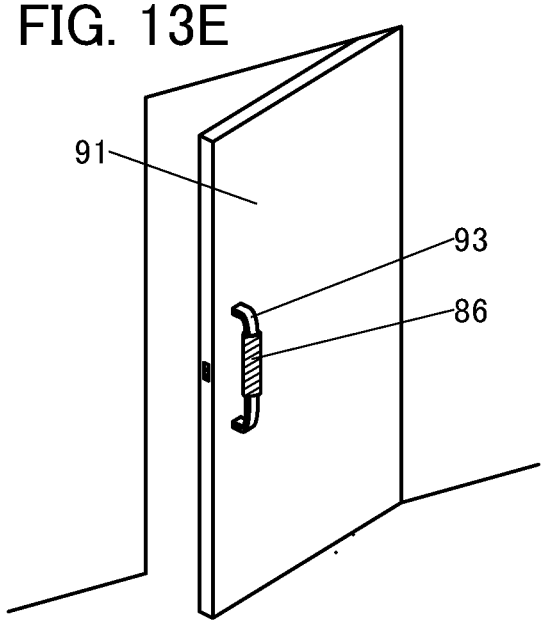

FIG. 13D shows a state where the user grasps the door knob 93, whereby the authentication portion 86 and the hand 52 are in contact with each other. As described above, the authentication portion 86 performs capturing a vein image of the hand 52 of the user and comparison. When authentication is approved as a result of the comparison, an authentication signal is transmitted from the authentication portion 86 to the external driver circuit 87, and the external driver circuit 87 transmits an unlocking signal to the electronic lock 95. The electronic lock 95 activates the bolt 96 to unlock the door 91, thereby enabling the door to be opened (FIG. 13E). The authentication device 80 is easily installed; it is easy to install the authentication device 80 on the existing door for example, and enhancement of security is possible.

Although FIG. 13A to FIG. 13E each illustrate the door knob 93 having such a shape as to be grasped in the longitudinal direction, the door knob 93 on which the authentication device of one embodiment of the present invention can be installed is not limited to the shape. For example, as illustrated in FIG. 14A1 and FIG. 14A2, the door knob 93 having such a shape as to be grasped laterally can be favorably used. For example, as illustrated in FIG. 14B1 and FIG. 14B2, the door knob 93 having a cylindrical shape can be favorably used.

The authentication device of one embodiment of the present invention can be installed in an automobile. FIG. 14C shows an example in which the authentication portion 86 is installed on a door 97 of an automobile 5700. The external driver circuit 87 is provided in a control portion (not illustrated) of the automobile 5700. The door 97 of the automobile 5700 may have a curved surface. The authentication portion 86 has flexibility and includes the adhesive layer 57 on its surface, thereby being able to be easily installed on the door 97 with a curved surface. When a user touches the authentication portion 86 with the hand 52, a vein image of the hand 52 of the user is captured and compared by the authentication portion 86. When authentication is approved as a result of the comparison, the authentication portion 86 transmits an authentication signal to the external driver circuit 87, and the external driver circuit 87 transmits an authentication signal to the control portion of the automobile 5700. The control portion of the automobile 5700 activates the lock of the door knob 98 to unlock the door, thereby enabling the door 97 to be opened. Furthermore, the control portion of the automobile 5700 may be made into a state enabling the engine to be started when the authentication signal is received.

The portion where the authentication portion 86 is installed is not limited to the door of the automobile but may be installed on a dashboard or a steering wheel, thereby causing a state enabling the engine be started when authentication is approved.

At least part of the structure examples, the drawings corresponding thereto, and the like exemplified in this embodiment can be implemented in combination with the other structure examples, the other drawings, and the like as appropriate.

At least part of this embodiment can be implemented in combination with the other embodiments described in this specification as appropriate.

Embodiment 3

In this embodiment, an authentication device of one embodiment of the present invention will be described with reference to FIG. 15 to FIG. 19.

A more detailed structure of the authentication device of one embodiment of the present invention will be described below with reference to FIG. 15 and FIG. 16.

[Authentication Device 80A]

Figure 15A:
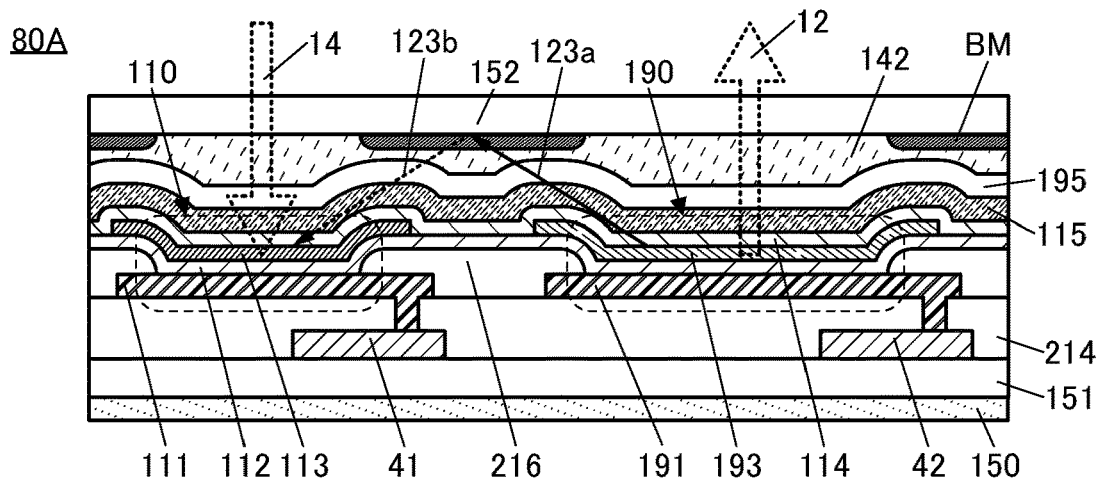
FIG. 15A, FIG. 15B, and FIG. 15C are cross-sectional views each illustrating an example of an authentication device.

FIG. 15A illustrates a cross-sectional view of an authentication device 80A.

The authentication device 80A includes a light-receiving element 110 and a light-emitting element 190.

The light-receiving element 110 includes a pixel electrode 111, a common layer 112, an active layer 113, a common layer 114, and a common electrode 115.

The light-emitting element 190 includes a pixel electrode 191, the common layer 112, a light-emitting layer 193, the common layer 114, and the common electrode 115.

The pixel electrode 111, the pixel electrode 191, the common layer 112, the active layer 113, the light-emitting layer 193, the common layer 114, and the common electrode 115 may each have a single-layer structure or a stacked-layer structure.

The pixel electrode 111 and the pixel electrode 191 are positioned over an insulating layer 214. The pixel electrode 111 and the pixel electrode 191 can be formed using the same material in the same step.

The common layer 112 is positioned over the pixel electrode 111 and the pixel electrode 191. The common layer 112 is shared by the light-receiving element 110 and the light-emitting element 190.

The active layer 113 overlaps with the pixel electrode 111 with the common layer 112 therebetween. The light-emitting layer 193 overlaps with the pixel electrode 191 with the common layer 112 therebetween. The active layer 113 contains a first organic compound, and the light-emitting layer 193 contains a second organic compound that is different from the first organic compound.

The common layer 114 is positioned over the common layer 112, the active layer 113, and the light-emitting layer 193. The common layer 114 is a layer shared by the light-receiving element 110 and the light-emitting element 190.

The common electrode 115 includes a portion overlapping with the pixel electrode 111 with the common layer 112, the active layer 113, and the common layer 114 therebetween. The common electrode 115 further includes a portion overlapping with the pixel electrode 191 with the common layer 112, the light-emitting layer 193, and the common layer 114 therebetween. The common electrode 115 is a layer shared by the light-receiving element 110 and the light-emitting element 190.

In the authentication device of this embodiment, an organic compound is used for the active layer 113 of the light-receiving element 110. In the light-receiving element 110, the layers other than the active layer 113 can be common to the layers in the light-emitting element 190 (the EL element). Therefore, the light-receiving element 110 can be formed concurrently with the formation of the light-emitting element 190 only by adding a step of depositing the active layer 113 in the manufacturing process of the light-emitting element 190. The light-emitting element 190 and the light-receiving element 110 can be formed over one substrate. Accordingly, the light-receiving element 110 can be incorporated into the authentication device without a significant increase in the number of manufacturing steps.

The authentication device 80A shows an example in which the light-receiving element 110 and the light-emitting element 190 have a common structure except that the active layer 113 of the light-receiving element 110 and the light-emitting layer 193 of the light-emitting element 190 are separately formed. Note that the structures of the light-receiving element 110 and the light-emitting element 190 are not limited thereto. The light-receiving element 110 and the light-emitting element 190 may include a separately formed layer other than the active layer 113 and the light-emitting layer 193 (see an authentication device 80D, an authentication device 80E, and an authentication device 80F described later). The light-receiving element 110 and the light-emitting element 190 preferably include at least one layer used in common (common layer). Thus, the light-receiving element 110 can be incorporated into the authentication device without a significant increase in the number of manufacturing steps.

The authentication device 80A includes the light-receiving element 110, the light-emitting element 190, a transistor 41, a transistor 42, and the like between a pair of substrates (a substrate 151 and a substrate 152).

An adhesive layer 150 is provided on the outer side of the substrate 151. The authentication device 80A can be fixed to an object with the adhesive layer 150. As the adhesive layer 150, an adhesive capable of being peeled off may be used. Furthermore, an adhesive capable of reattachment after being peeled may be employed. As the adhesive layer 150, an epoxy resin, an acrylic resin, a silicone resin, a phenol resin, a polyimide resin, an imide resin, a PVC (polyvinyl chloride) resin, a PVB (polyvinyl butyral) resin, an EVA (ethylene vinyl acetate) resin, or the like can be used. In particular, a material with low moisture permeability, such as an epoxy resin, is preferred. Alternatively, a two-component resin may be used. An adhesive sheet or the like may be used.

In the light-receiving element 110, the common layer 112, the active layer 113, and the common layer 114 that are positioned between the pixel electrode 111 and the common electrode 115 can each be referred to as an organic layer (a layer containing an organic compound). The pixel electrode 111 preferably has a function of reflecting infrared light. An end portion of the pixel electrode 111 is covered with a bank 216. The common electrode 115 has a function of transmitting infrared light.

The light-receiving element 110 has a function of sensing light. Specifically, the light-receiving element 110 is a light-receiving element that receives infrared light 14 incident from the outside of the authentication device 80A and converts it into an electric signal. The infrared light 14 can also be expressed as light that is emitted by the light-emitting element 190 and then reflected by an object. The infrared light 14 may enter the light-receiving element 110 through a lens (not illustrated).

A light-blocking layer BM is provided on a surface of the substrate 152 on the substrate 151 side. The light-blocking layer BM has openings at a position overlapping with the light-receiving element 110 and at a position overlapping with the light-emitting element 190. Providing the light-blocking layer BM can control the range where the light-receiving element 110 senses light.

For the light-blocking layer BM, a material that blocks light emitted from the light-emitting element can be used. The light-blocking layer BM preferably absorbs infrared light. As the light-blocking layer BM, a black matrix can be formed using a metal material or a resin material containing pigment (e.g., carbon black) or dye, for example.

Here, the light-receiving element 110 senses light that is emitted by the light-emitting element 190 and then reflected by an object. However, in some cases, light emitted from the light-emitting element 190 is reflected inside the authentication device 80A and enters the light-receiving element 110 without via an object. The light-blocking layer BM can reduce the influence of such stray light. For example, in the case where the light-blocking layer BM is not provided, light 123a emitted from the light-emitting element 190 is reflected by the substrate 152 and reflected light 123b is incident on the light-receiving element 110 in some cases. Providing the light-blocking layer BM can inhibit entry of the reflected light 123b into the light-receiving element 110. Consequently, noise can be reduced, and the sensitivity of a sensor using the light-receiving element 110 can be increased.

In the light-emitting element 190, the common layer 112, the light-emitting layer 193, and the common layer 114 that are positioned between the pixel electrode 191 and the common electrode 115 can each be referred to as an EL layer. The pixel electrode 191 preferably has a function of reflecting infrared light. An end portion of the pixel electrode 191 is covered with the bank 216. The pixel electrode 111 and the pixel electrode 191 are electrically isolated from each other by the bank 216. The common electrode 115 has a function of transmitting infrared light.

The light-emitting element 190 has a function of emitting infrared light. Specifically, the light-emitting element 190 is an electroluminescent element that emits light to the substrate 152 side by applying a voltage between the pixel electrode 191 and the common electrode 115 (see infrared light 12).

It is preferable that the light-emitting layer 193 be formed not to overlap with a light-receiving region of the light-receiving element 110. Accordingly, it is possible to inhibit the light-emitting layer 193 from absorbing the infrared light 14, so that the amount of light with which the light-receiving element 110 is irradiated can be increased.

The pixel electrode 111 is electrically connected to a source or a drain of the transistor 41 through an opening provided in the insulating layer 214. An end portion of the pixel electrode 111 is covered with the bank 216.

The pixel electrode 191 is electrically connected to a source or a drain of the transistor 42 through an opening provided in the insulating layer 214. An end portion of the pixel electrode 191 is covered with the bank 216. The transistor 42 has a function of controlling the driving of the light-emitting element 190.

The transistor 41 and the transistor 42 are on and in contact with the same layer (the substrate 151 in FIG. 15A).

At least part of a circuit electrically connected to the light-receiving element 110 is preferably formed using the same material in the same steps as a circuit electrically connected to the light-emitting element 190. Accordingly, the thickness of the authentication device can be smaller and the manufacturing process can be simpler than those in the case where the two circuits are separately formed.

The light-receiving element 110 and the light-emitting element 190 are preferably covered with a protective layer 195. In FIG. 15A, the protective layer 195 is provided on and in contact with the common electrode 115. Providing the protective layer 195 can inhibit entry of impurities such as water into the light-receiving element 110 and the light-emitting element 190, so that the reliability of the light-receiving element 110 and the light-emitting element 190 can be increased. The protective layer 195 and the substrate 152 are bonded to each other with an adhesive layer 142.

[Authentication Device 80B]

Figure 15B:
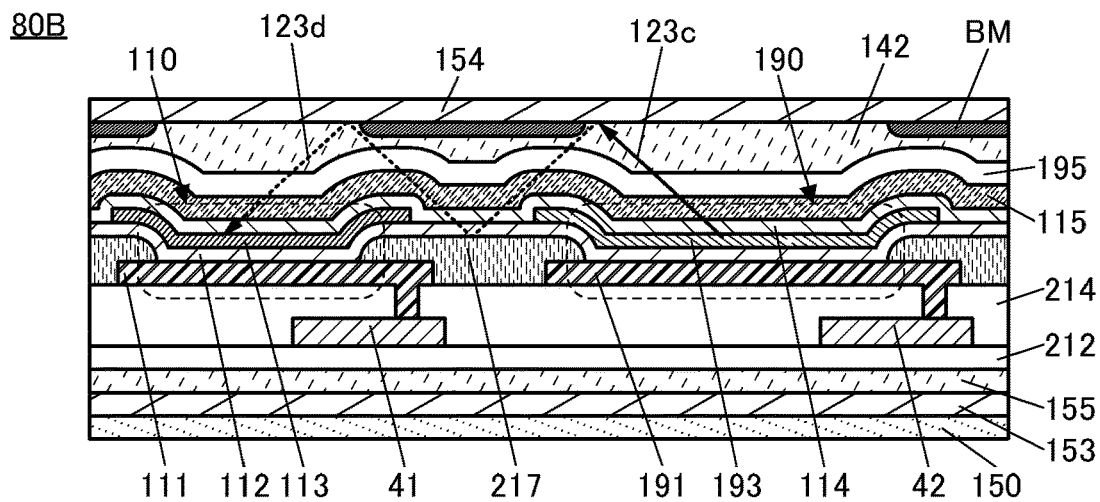

FIG. 15B illustrates a cross-sectional view of an authentication device 80B. Note that in the description of the authentication device below, components similar to those of the above-described authentication device are not described in some cases.

The authentication device 80B illustrated in FIG. 15B differs from the authentication device 80A in that the substrate 151, the substrate 152, and the bank 216 are not included and a substrate 153, a substrate 154, an adhesive layer 155, an insulating layer 212, and a bank 217 are included.

The adhesive layer 150 is provided on the outer side of the substrate 153. The authentication device 80B can be fixed to an object with the adhesive layer 150.

The substrate 153 and the insulating layer 212 are bonded to each other with the adhesive layer 155. The substrate 154 and the protective layer 195 are bonded to each other with the adhesive layer 142.

The authentication device 80B has a structure formed in such a manner that the insulating layer 212, the transistor 41, the transistor 42, the light-receiving element 110, the light-emitting element 190, and the like that are formed over a formation substrate are transferred onto the substrate 153. The substrate 153 and the substrate 154 are preferably flexible. Accordingly, the flexibility of the authentication device 80B can be increased. For example, a resin is preferably used for each of the substrate 153 and the substrate 154.

For each of the substrate 153 and the substrate 154, a polyester resin such as polyethylene terephthalate (PET) or polyethylene naphthalate (PEN), a polyacrylonitrile resin, an acrylic resin, a polyimide resin, a polymethyl methacrylate resin, a polycarbonate (PC) resin, a polyether sulfone (PES) resin, a polyamide resin (e.g., nylon or aramid), a polysiloxane resin, a cycloolefin resin, a polystyrene resin, a polyamide-imide resin, a polyurethane resin, a polyvinyl chloride resin, a polyvinylidene chloride resin, a polypropylene resin, a polytetrafluoroethylene (PTFE) resin, an ABS resin, or cellulose nanofiber can be used, for example. Glass that is thin enough to have flexibility may be used for one or both of the substrate 153 and the substrate 154.

As the substrate included in the authentication device of this embodiment, a film having high optical isotropy may be used. Examples of a highly optically isotropic film include a triacetyl cellulose (TAC, also referred to as cellulose triacetate) film, a cycloolefin polymer (COP) film, a cycloolefin copolymer (COC) film, and an acrylic film.

The bank 217 preferably absorbs light emitted from the light-emitting element. As the bank 217, a black matrix can be formed using a resin material containing a pigment or dye, for example. Moreover, the bank 217 can be formed of a colored insulating layer by using a brown resist material.

In some cases, light 123c emitted from the light-emitting element 190 is reflected by the substrate 152 and the bank 217 and reflected light 123d is incident on the light-receiving element 110. In other cases, the light 123c passes through the bank 217 and is reflected by a transistor, a wiring, or the like, and thus reflected light is incident on the light-receiving element 110, in some cases. When the bank 217 absorbs the light 123c, the reflected light 123d can be inhibited from being incident on the light-receiving element 110. Consequently, noise can be reduced, and the sensitivity of a sensor using the light-receiving element 110 can be increased.

The bank 217 preferably absorbs at least light having a wavelength that is sensed by the light-receiving element 110. For example, in the case where the light-receiving element 110 senses green light emitted from the light-emitting element 190, the bank 217 preferably absorbs at least green light. For example, when the bank 217 includes a red color filter, the green light 123c can be absorbed and thus the reflected light 123d can be inhibited from being incident on the light-receiving element 110.

[Authentication Device 80C]

Figure 15C:
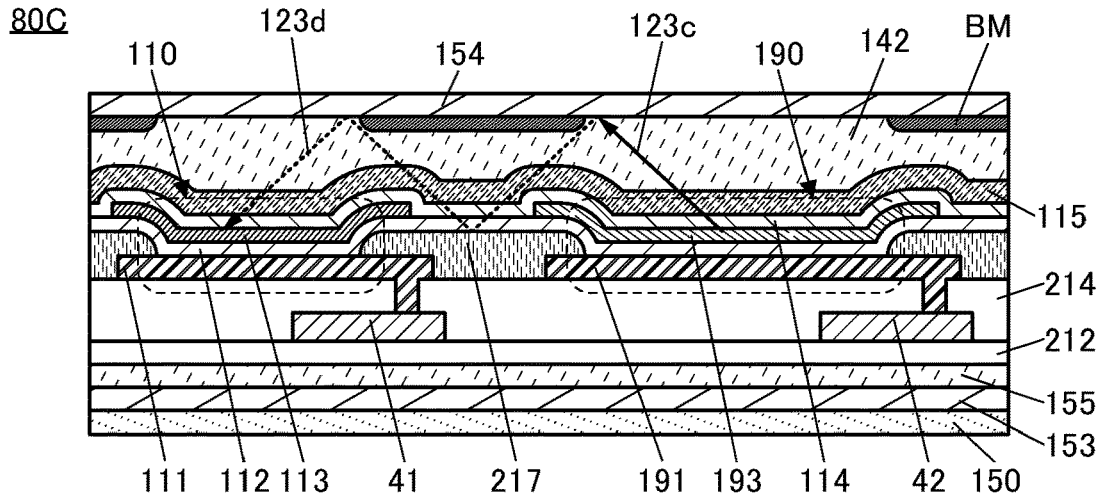

FIG. 15C illustrates a cross-sectional view of an authentication device 80C.

The authentication device 80C differs from the authentication device 80B in that the protective layer 195 is not provided over the light-receiving element 110 and the light-emitting element 190. In the authentication device 80C, the common electrode 115 and the substrate 152 are bonded to each other with the adhesive layer 142.

[Authentication Device 80D, Authentication Device 80E, Authentication Device 80F]

Figure 16A:
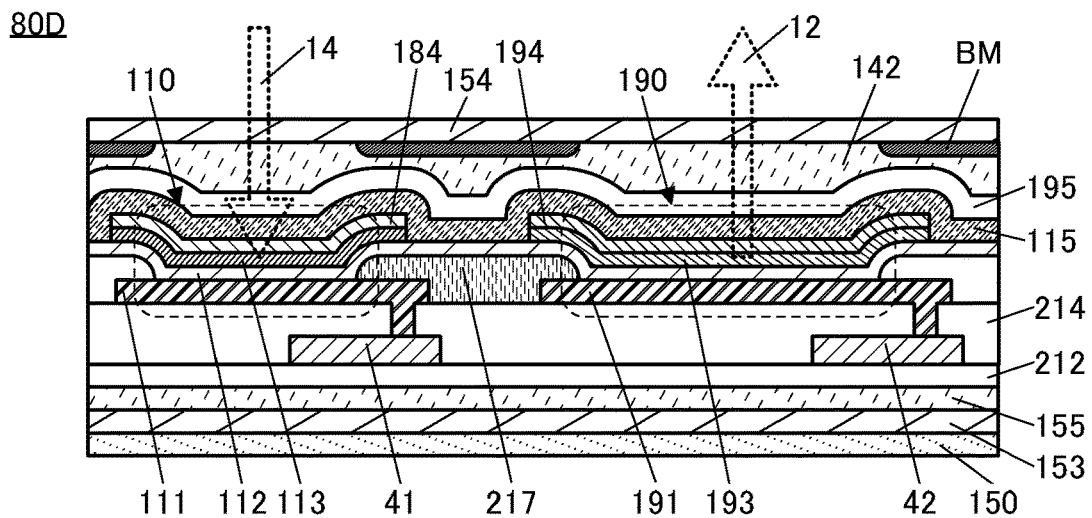
FIG. 16A, FIG. 16B, and FIG. 16C are cross-sectional views each illustrating an example of an authentication device.
Figure 16B:
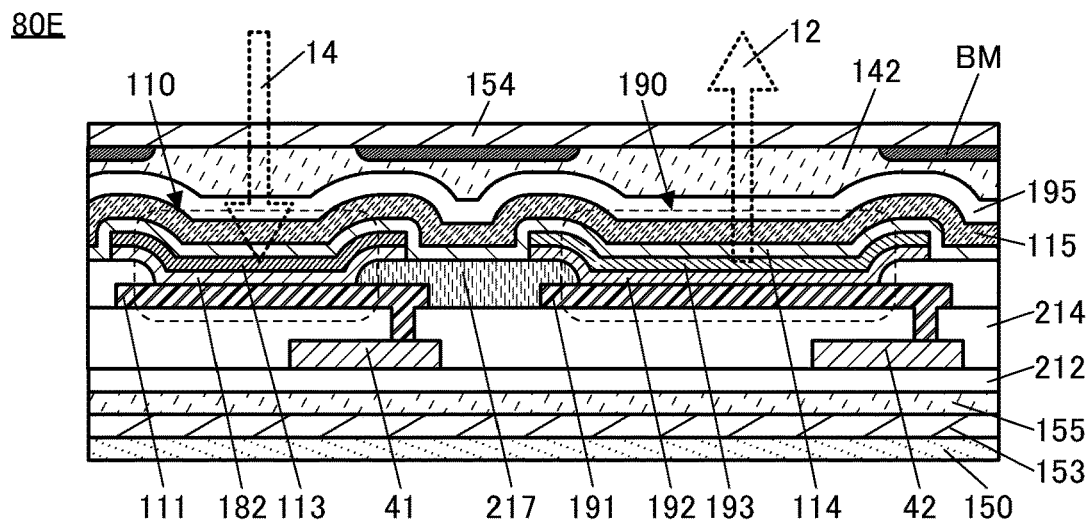
Figure 16C:
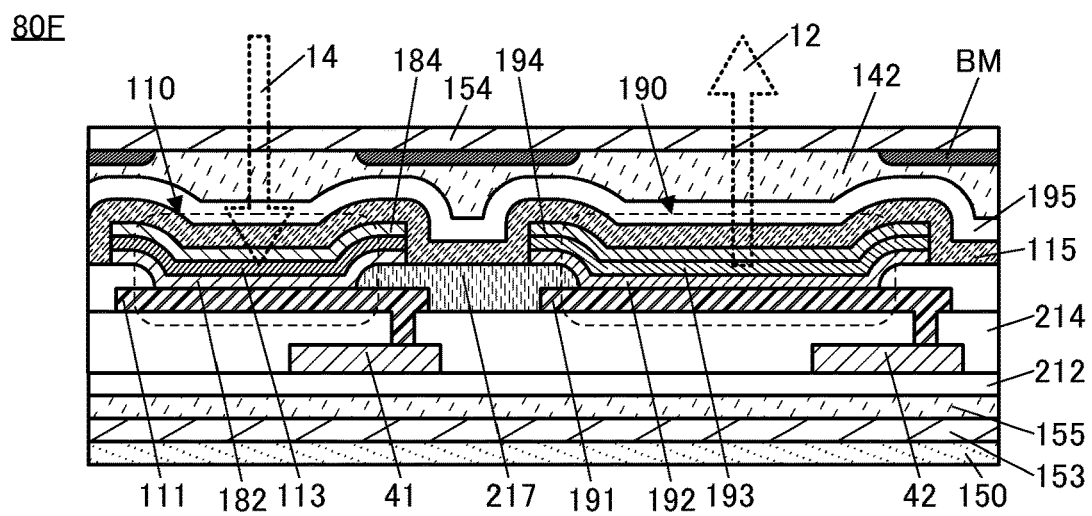

FIG. 16A illustrates a cross-sectional view of the authentication device 80D, FIG. 16B illustrates a cross-sectional view of the authentication device 80E, and FIG. 16C illustrates a cross-sectional view of the authentication device 80F.

The authentication device 80D differs from the authentication device 80B in that the common layer 114 is not included and a buffer layer 184 and a buffer layer 194 are included. The buffer layer 184 and the buffer layer 194 may each have a single-layer structure or a stacked-layer structure.

In the authentication device 80D, the light-receiving element 110 includes the pixel electrode 111, the common layer 112, the active layer 113, the buffer layer 184, and the common electrode 115. In the authentication device 80D, the light-emitting element 190 includes the pixel electrode 191, the common layer 112, the light-emitting layer 193, the buffer layer 194, and the common electrode 115.

The authentication device 80E differs from the authentication device 80B in that the common layer 112 is not included and a buffer layer 182 and a buffer layer 192 are included. The buffer layer 182 and the buffer layer 192 may each have a single-layer structure or a stacked-layer structure.

In the authentication device 80E, the light-receiving element 110 includes the pixel electrode 111, the buffer layer 182, the active layer 113, the common layer 114, and the common electrode 115. Furthermore, in the authentication device 80E, the light-emitting element 190 includes the pixel electrode 191, the buffer layer 192, the light-emitting layer 193, the common layer 114, and the common electrode 115.

The authentication device 80F differs from the authentication device 80B in that the common layer 112 and the common layer 114 are not included and the buffer layer 182, the buffer layer 184, the buffer layer 192, and the buffer layer 194 are included.

In the authentication device 80F, the light-receiving element 110 includes the pixel electrode 111, the buffer layer 182, the active layer 113, the buffer layer 184, and the common electrode 115. Furthermore, in the authentication device 80F, the light-emitting element 190 includes the pixel electrode 191, the buffer layer 192, the light-emitting layer 193, the buffer layer 194, and the common electrode 115.

Other layers as well as the active layer 113 and the light-emitting layer 193 can be formed separately when the light-receiving element 110 and the light-emitting element 190 are manufactured.

In the authentication device 80D, an example is shown in which the buffer layer 184 between the common electrode 115 and the active layer 113 and the buffer layer 194 between the common electrode 115 and the light-emitting layer 193 are formed separately. As the buffer layer 194, one or both of an electron-injection layer and an electron-transport layer can be formed, for example.

In the authentication device 80E, an example is shown in which the buffer layer 182 between the pixel electrode 111 and the active layer 113 and the buffer layer 192 between the pixel electrode 191 and the light-emitting layer 193 are formed separately. As the buffer layer 192, one or both of a hole-injection layer and a hole-transport layer can be formed, for example.

In the authentication device 80F, an example is shown in which in each of the light-receiving element 110 and the light-emitting element 190, a common layer is not provided between the pair of electrodes (the pixel electrode 111 or the pixel electrode 191 and the common electrode 115). The light-receiving element 110 and the light-emitting element 190 included in the authentication device 80F can be manufactured in the following manner: the pixel electrode 111 and the pixel electrode 191 are formed over the insulating layer 214 using the same material in the same step; the buffer layer 182, the active layer 113, and the buffer layer 184 are formed over the pixel electrode 111; the buffer layer 192, the light-emitting layer 193, and the buffer layer 194 are formed over the pixel electrode 191; and then, the common electrode 115 is formed to cover the pixel electrode 111, the buffer layer 182, the active layer 113, the buffer layer 184, the pixel electrode 191, the buffer layer 192, the light-emitting layer 193, and the buffer layer 194. Note that the manufacturing order of the stacked-layer structure of the buffer layer 182, the active layer 113, and the buffer layer 184 and the stacked-layer structure of the buffer layer 192, the light-emitting layer 193, and the buffer layer 194 is not particularly limited. For example, after the buffer layer 182, the active layer 113, and the buffer layer 184 are deposited, the buffer layer 192, the light-emitting layer 193, and the buffer layer 194 may be formed. In contrast, the buffer layer 192, the light-emitting layer 193, and the buffer layer 194 may be formed before the buffer layer 182, the active layer 113, and the buffer layer 184 are deposited. Alternatively, alternate deposition of the buffer layer 182, the buffer layer 192, the active layer 113, and the light-emitting layer 193 in this order may be performed.

A more detailed structure of the authentication device of one embodiment of the present invention will be described below with reference to FIG. 14 to FIG. 19.

[Authentication Device 100A]

Figure 17:
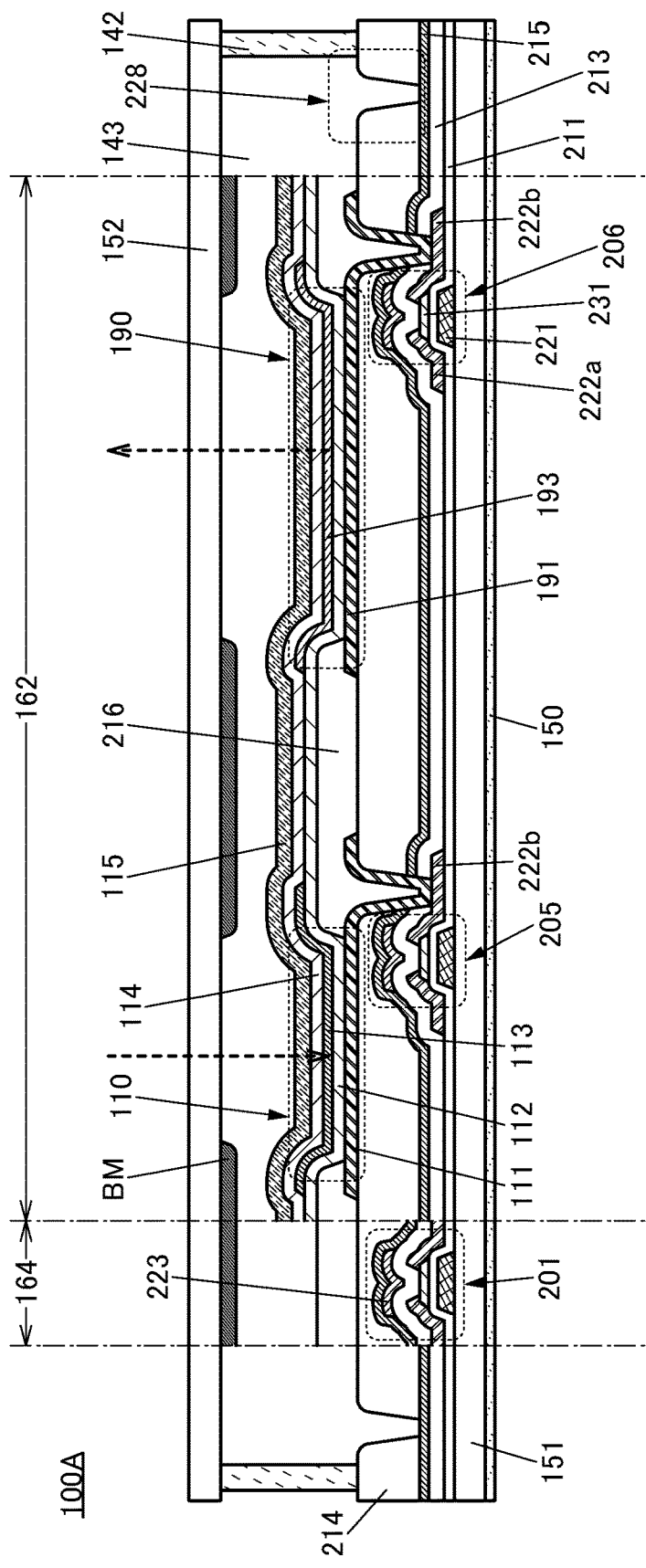
FIG. 17 is a cross-sectional view illustrating an example of an authentication device.

FIG. 17 illustrates a cross-sectional view of an authentication device 100A.

The authentication device 100A has a structure in which the substrate 152 and the substrate 151 are bonded to each other.

The authentication device 100A includes a pixel array 162, a circuit 164, and the like. FIG. 17 illustrates an example of cross sections of a part of a region including the circuit 164, a part of a region including the pixel array 162, and a part of a region including an end portion in the authentication device 100A.

As the circuit 164, for example, the circuit 22, the circuit 23, and the circuit 28 described in Embodiment 1 can be used. As the circuit 164, the control portion 82, the input/output portion 85, and the memory portion 83 in Embodiment 2 can be used, for example. When the pixel array 162 and the circuit 164 are formed over the same substrate, a semiconductor device separately formed with a silicon wafer or the like as a circuit is not needed, so that the number of components of the authentication device can be reduced.

The authentication device 100A illustrated in FIG. 17 includes a transistor 201, a transistor 205, a transistor 206, the light-emitting element 190, the light-receiving element 110, and the like between the substrate 151 and the substrate 152.

The substrate 152 and the insulating layer 214 are bonded to each other with the adhesive layer 142. A solid sealing structure, a hollow sealing structure, or the like can be employed to seal the light-emitting element 190 and the light-receiving element 110. In FIG. 17, a hollow sealing structure is employed in which a space 143 surrounded by the substrate 152, the adhesive layer 142, and the insulating layer 214 is filled with an inert gas (e.g., nitrogen or argon). The adhesive layer 142 may be provided to overlap with the light-emitting element 190. The space 143 surrounded by the substrate 152, the adhesive layer 142, and the insulating layer 214 may be filled with a resin different from that of the adhesive layer 142.

The light-emitting element 190 has a stacked-layer structure in which the pixel electrode 191, the common layer 112, the light-emitting layer 193, the common layer 114, and the common electrode 115 are stacked in this order from the insulating layer 214 side. The pixel electrode 191 is connected to a conductive layer 222b included in the transistor 206 through an opening provided in the insulating layer 214. The transistor 206 has a function of controlling the driving of the light-emitting element 190. An end portion of the pixel electrode 191 is covered with the bank 216. The pixel electrode 191 includes a material that reflects infrared light, and the common electrode 115 includes a material that transmits infrared light.

The light-receiving element 110 has a stacked-layer structure in which the pixel electrode 111, the common layer 112, the active layer 113, the common layer 114, and the common electrode 115 are stacked in that order from the insulating layer 214 side. The pixel electrode 111 is electrically connected to the conductive layer 222b included in the transistor 205 through an opening provided in the insulating layer 214. An end portion of the pixel electrode 111 is covered with the bank 216. The pixel electrode 111 includes a material that reflects infrared light, and the common electrode 115 includes a material that transmits infrared light.

Light emitted from the light-emitting element 190 is emitted to the substrate 152 side. Light enters the light-receiving element 110 through the substrate 152 and the space 143. For the substrate 152, a material having a high infrared-light-transmitting property is preferably used.

The pixel electrode 111 and the pixel electrode 191 can be formed using the same material in the same step. The common layer 112, the common layer 114, and the common electrode 115 are used in both the light-receiving element 110 and the light-emitting element 190. The light-receiving element 110 and the light-emitting element 190 can have common components except the active layer 113 and the light-emitting layer 193. Thus, the light-receiving element 110 can be incorporated into the authentication device 100A without a significant increase in the number of manufacturing steps.

A light-blocking layer BM is provided on a surface of the substrate 152 on the substrate 151 side. The light-blocking layer BM has openings at a position overlapping with the light-receiving element 110 and at a position overlapping with the light-emitting element 190. Providing the light-blocking layer BM can control the range where the light-receiving element 110 senses light. Furthermore, with the light-blocking layer BM, light can be prevented from directly entering the light-receiving element 110 from the light-emitting element 190 without through an object. Hence, a sensor with less noise and high sensitivity can be obtained.

The transistor 201, the transistor 205, and the transistor 206 are formed over the substrate 151. These transistors can be fabricated using the same material in the same process.

An insulating layer 211, an insulating layer 213, an insulating layer 215, and the insulating layer 214 are provided in this order over the substrate 151. Parts of the insulating layer 211 function as gate insulating layers of the transistors. Parts of the insulating layer 213 function as gate insulating layers of the transistors. The insulating layer 215 is provided to cover the transistors. The insulating layer 214 is provided to cover the transistors and has a function of a planarization layer. Note that the number of gate insulating layers and the number of insulating layers covering the transistor are not limited and either a single layer or two or more layers may be employed.

A material through which impurities such as water and hydrogen do not easily diffuse is preferably used for at least one of the insulating layers that cover the transistors. Thus, such an insulating layer can serve as a barrier layer. Such a structure can effectively inhibit diffusion of impurities into the transistors from the outside and increase the reliability of the authentication device.

An inorganic insulating film is preferably used as each of the insulating layer 211, the insulating layer 213, and the insulating layer 215. As the inorganic insulating film, for example, an inorganic insulating film such as a silicon nitride film, a silicon oxynitride film, a silicon oxide film, a silicon nitride oxide film, an aluminum oxide film, or an aluminum nitride film can be used. A hafnium oxide film, an yttrium oxide film, a zirconium oxide film, a gallium oxide film, a tantalum oxide film, a magnesium oxide film, a lanthanum oxide film, a cerium oxide film, a neodymium oxide film, or the like may also be used. A stack including two or more of the above insulating films may also be used.

Here, an organic insulating film often has a lower barrier property than an inorganic insulating film. Therefore, the organic insulating film preferably has an opening in the vicinity of an end portion of the authentication device 100A. This can inhibit entry of impurities from the end portion of the authentication device 100A through the organic insulating film. Alternatively, the organic insulating film may be formed so that an end portion of the organic insulating film is positioned on the inner side than a position of the end portion of the authentication device 100A, to prevent the organic insulating film from being exposed at the end portion of the authentication device 100A.

An organic insulating film is suitable for the insulating layer 214 functioning as a planarization layer. Other examples of materials which can be used for the organic insulating film include an acrylic resin, a polyimide resin, an epoxy resin, a polyamide resin, a polyimide-amide resin, a siloxane resin, a benzocyclobutene-based resin, a phenol resin, and precursors of these resins.

In a region 228 illustrated in FIG. 17, an opening is formed in the insulating layer 214. This can inhibit entry of impurities into the pixel array 162 from the outside through the insulating layer 214 even when an organic insulating film is used as the insulating layer 214. Thus, the reliability of the authentication device 100A can be increased.

Each of the transistor 201, the transistor 205, and the transistor 206 includes a conductive layer 221 functioning as a gate, the insulating layer 211 functioning as the gate insulating layer, a conductive layer 222a and the conductive layer 222b functioning as a source and a drain, a semiconductor layer 231, the insulating layer 213 functioning as the gate insulating layer, and a conductive layer 223 functioning as a gate. Here, a plurality of layers obtained by processing the same conductive film are shown with the same hatching pattern. The insulating layer 211 is positioned between the conductive layer 221 and the semiconductor layer 231. The insulating layer 213 is positioned between the conductive layer 223 and the semiconductor layer 231.

There is no particular limitation on the structure of the transistors included in the authentication device of this embodiment. For example, a planar transistor, a staggered transistor, or an inverted staggered transistor can be used. A top-gate or bottom-gate transistor structure may be employed. Alternatively, gates may be provided above and below a semiconductor layer where a channel is formed.

The structure in which the semiconductor layer where a channel is formed is provided between two gates is used for the transistor 201, the transistor 205, and the transistor 206. The two gates may be connected to each other and supplied with the same signal to operate the transistor. Alternatively, by supplying a potential for controlling the threshold voltage to one of the two gates and a potential for driving to the other, the threshold voltage of the transistor may be controlled.

There is no particular limitation on the crystallinity of a semiconductor material used for the transistors, and an amorphous semiconductor or a semiconductor having crystallinity (a microcrystalline semiconductor, a polycrystalline semiconductor, a single-crystal semiconductor, or a semiconductor partly including crystal regions) may be used. A semiconductor having crystallinity is preferably used, in which case deterioration of the transistor characteristics can be suppressed.

It is preferable that a semiconductor layer of a transistor contain a metal oxide (also referred to as an oxide semiconductor). Alternatively, the semiconductor layer of the transistor may contain silicon. Examples of silicon include amorphous silicon and crystalline silicon (e.g., low-temperature polysilicon or single crystal silicon).

The semiconductor layer preferably contains indium, M (M is one or more kinds selected from gallium, aluminum, silicon, boron, yttrium, tin, copper, vanadium, beryllium, titanium, iron, nickel, germanium, zirconium, molybdenum, lanthanum, cerium, neodymium, hafnium, tantalum, tungsten, and magnesium), and zinc, for example. Specifically, M is preferably one or more kinds selected from aluminum, gallium, yttrium, and tin.

It is particularly preferable to use an oxide containing indium (In), gallium (Ga), and zinc (Zn) (also referred to as IGZO) for the semiconductor layer.

In the case where the semiconductor layer is an In-M-Zn oxide, a sputtering target used for depositing the In-M-Zn oxide preferably has the atomic proportion of In higher than or equal to the atomic proportion of M. Examples of the atomic ratio of the metal elements in such a sputtering target include In:M:Zn=1:1:1, In:M:Zn=1:1:1.2, In:M:Zn=2:1:3, In:M:Zn=3:1:2, In:M:Zn=4:2:3, In:M:Zn=4:2:4.1, In:M:Zn=5:1:6, In:M:Zn=5:1:7, In:M:Zn=5:1:8, In:M:Zn=6:1:6, and In:M:Zn=5:2:5.

A target containing a polycrystalline oxide is preferably used as the sputtering target, in which case the semiconductor layer having crystallinity is easily formed. Note that the atomic ratio between metal elements in the deposited semiconductor layer may vary from the above atomic ratio between metal elements in the sputtering target in a range of ±40%. For example, in the case where the composition of a sputtering target used for the semiconductor layer is In:Ga:Zn=4:2:4.1 [atomic ratio], the composition of the semiconductor layer to be deposited is in some cases in the neighborhood of In:Ga:Zn=4:2:3 [atomic ratio].

Note that when the atomic ratio is described as In:Ga:Zn=4:2:3 or as being in the neighborhood thereof, the case is included where the atomic proportion of Ga is greater than or equal to 1 and less than or equal to 3 and the atomic proportion of Zn is greater than or equal to 2 and less than or equal to 4 with the atomic proportion of In being 4. When the atomic ratio is described as In:Ga:Zn=5:1:6 or as being in the neighborhood thereof, the case is included where the atomic proportion of Ga is greater than 0.1 and less than or equal to 2 and the atomic proportion of Zn is greater than or equal to 5 and less than or equal to 7 with the atomic proportion of In being 5. When the atomic ratio is described as In:Ga:Zn=1:1:1 or as being in the neighborhood thereof, the case is included where the atomic proportion of Ga is greater than 0.1 and less than or equal to 2 and the atomic proportion of Zn is greater than 0.1 and less than or equal to 2 with the atomic proportion of In being 1.

The transistor included in the circuit 164 and the transistor included in the pixel array 162 may have the same structure or different structures. One structure or two or more kinds of structures may be employed for a plurality of transistors included in the circuit 164. Similarly, one structure or two or more kinds of structures may be employed for a plurality of transistors included in the pixel array 162.

The adhesive layer 150 is provided on the outer side of the substrate 151. The authentication device 100A can be fixed to an object with the adhesive layer 150.

Any of a variety of optical members can be arranged on the outer side of the substrate 152. Examples of the optical members include a polarizing plate, a retardation plate, a light diffusion layer (a diffusion film or the like), an anti-reflective layer, and a light-condensing film. Furthermore, an antistatic film preventing the attachment of dust, a water repellent film suppressing the attachment of stain, a hard coat film inhibiting generation of a scratch caused by the use, a shock absorption layer, or the like may be arranged on the outside of the substrate 152.

For each of the substrate 151 and the substrate 152, glass, quartz, ceramic, sapphire, a resin, or the like can be used. When a flexible material is used for the substrate 151 and the substrate 152, the flexibility of the authentication device can be increased.

As each of the adhesive layer 142 and the adhesive layer 150, a variety of curable adhesives such as a photocurable adhesive such as an ultraviolet curable adhesive, a reactive curable adhesive, a thermosetting adhesive, and an anaerobic adhesive can be used. Examples of these adhesives include an epoxy resin, an acrylic resin, a silicone resin, a phenol resin, a polyimide resin, an imide resin, a PVC resin, a PVB resin, and an EVA resin. In particular, a material with low moisture permeability, such as an epoxy resin, is preferred. Alternatively, a two-component resin may be used. An adhesive sheet or the like may be used.

The light-emitting element 190 may be a top emission, bottom emission, or dual emission light-emitting element, or the like. A conductive film that transmits infrared light is used as the electrode through which light is extracted. A conductive film that reflects infrared light is preferably used as the electrode through which no light is extracted.

The light-emitting element 190 includes at least the light-emitting layer 193. In addition to the light-emitting layer 193, the light-emitting element 190 may further include a layer containing a substance with a high hole-injection property, a layer containing a substance with a high hole-transport property, a layer containing a hole-blocking material, a layer containing a substance with a high electron-transport property, a layer containing a substance with a high electron-injection property, a layer containing a substance with a bipolar property (a substance with a high electron- and hole-transport property), or the like. For example, the common layer 112 preferably includes one or both of a hole-injection layer and a hole-transport layer. For example, the common layer 114 preferably includes one or both of an electron-transport layer and an electron-injection layer.

Either a low molecular compound or a high molecular compound can be used for the common layer 112, the light-emitting layer 193, and the common layer 114, and an inorganic compound may also be contained. The layers that constitute the common layer 112, the light-emitting layer 193, and the common layer 114 can each be formed by a method such as an evaporation method (including a vacuum evaporation method), a transfer method, a printing method, an inkjet method, or a coating method.

The light-emitting layer 193 may contain an inorganic compound such as quantum dots as a light-emitting material.

The active layer 113 of the light-receiving element 110 contains a semiconductor. Examples of the semiconductor include an inorganic semiconductor such as silicon and an organic semiconductor including an organic compound. This embodiment shows an example in which an organic semiconductor is used as the semiconductor contained in the active layer. The use of an organic semiconductor is preferable because the light-emitting layer 193 of the light-emitting element 190 and the active layer 113 of the light-receiving element 110 can be formed by the same method (e.g., a vacuum evaporation method) and thus the same manufacturing apparatus can be used.

Examples of an n-type semiconductor material included in the active layer 113 are electron-accepting organic semiconductor materials such as fullerene (e.g., $C_{60}$ and $C_{70}$) and derivatives thereof. As a p-type semiconductor material contained in the active layer 113, an electron-donating organic semiconductor material such as copper(II) phthalocyanine (CuPc) or tetraphenyldibenzoperiflanthene (DBP) can be given.

For example, the active layer 113 is preferably formed by co-evaporation of an n-type semiconductor and a p-type semiconductor.

As materials for a conductive layer such as a wiring or an electrode that forms an authentication device in addition to a gate, a source, and a drain of a transistor, metals such as aluminum, titanium, chromium, nickel, copper, yttrium, zirconium, molybdenum, silver, tantalum, and tungsten, or an alloy containing any of these metals as its main component can be given. A film containing any of these materials can be used in a single layer or as a stacked-layer structure.

As a light-transmitting conductive material, a conductive oxide such as indium oxide, indium tin oxide, indium zinc oxide, zinc oxide, or zinc oxide containing gallium, or graphene can be used. Alternatively, a metal material such as gold, silver, platinum, magnesium, nickel, tungsten, chromium, molybdenum, iron, cobalt, copper, palladium, or titanium, or an alloy material containing the metal material can be used. Further alternatively, a nitride of the metal material (e.g., titanium nitride) or the like may be used. Note that in the case of using the metal material or the alloy material (or the nitride thereof), the thickness is preferably set small enough to be able to transmit light. A stacked-layer film of any of the above materials can be used for the conductive layers. For example, when a stacked film of indium tin oxide and an alloy of silver and magnesium, or the like is used, the conductivity can be increased, which is preferable. They can also be used for conductive layers such as a variety of wirings and electrodes that constitute an authentication device, and conductive layers (conductive layers functioning as a pixel electrode or a common electrode) included in a display element.

As an insulating material that can be used for each insulating layer, for example, a resin such as an acrylic resin or an epoxy resin, and an inorganic insulating material such as silicon oxide, silicon oxynitride, silicon nitride oxide, silicon nitride, or aluminum oxide can be given.

[Authentication Device 100B]

Figure 18:
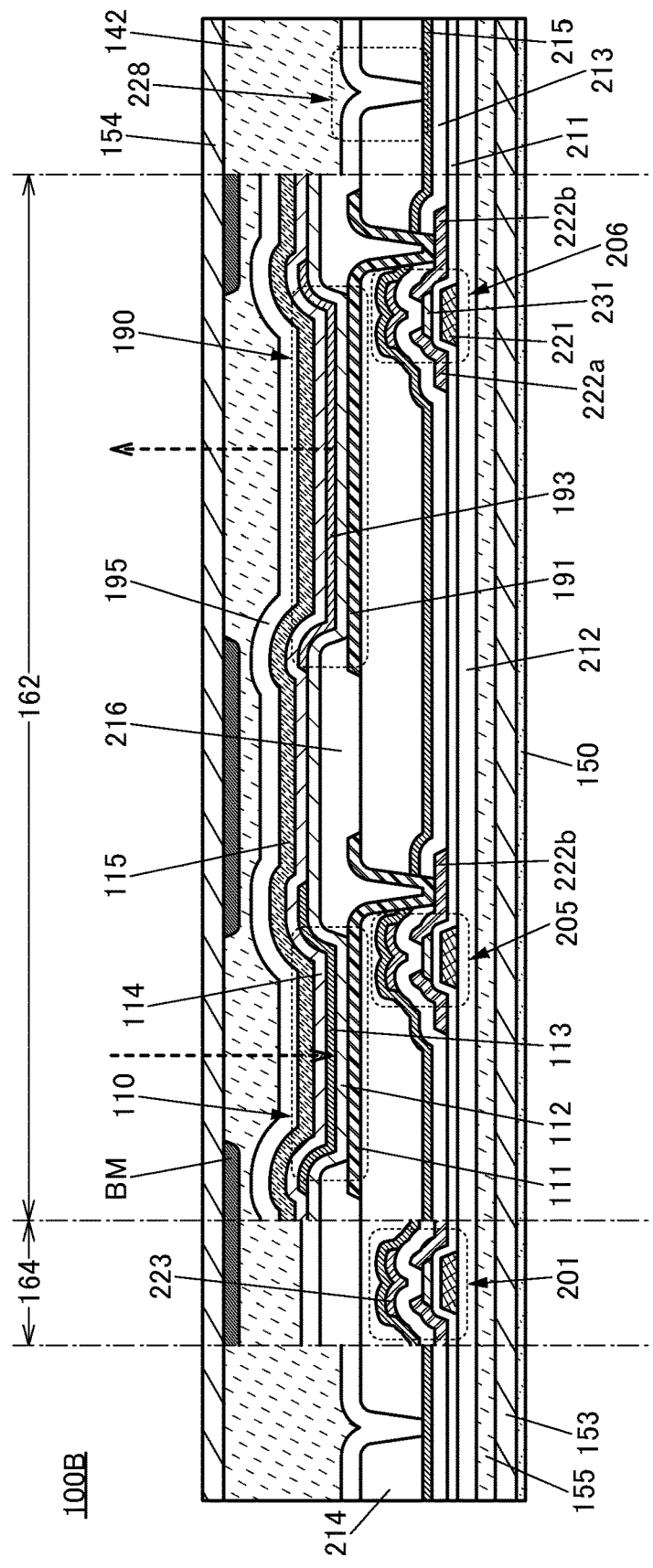
FIG. 18 is a cross-sectional view illustrating an example of an authentication device.

FIG. 18 illustrates a cross-sectional view of an authentication device 100B.

The authentication device 100B differs from the authentication device 100A mainly in that the substrate 151 and the substrate 152 are not included, the substrate 153, the substrate 154, the adhesive layer 155, and the insulating layer 212 are included, and the protective layer 195 is included.

The substrate 153 and the insulating layer 212 are bonded to each other with the adhesive layer 155. The substrate 154 and the protective layer 195 are bonded to each other with the adhesive layer 142. The adhesive layer 142 is provided to overlap with the light-receiving element 110 and the light-emitting element 190; that is, the authentication device 100B employs a solid sealing structure.

The authentication device 100B is formed in such a manner that the insulating layer 212, the transistor 208, the transistor 209, the light-receiving element 110, the light-emitting element 190, and the like that are formed over a formation substrate are transferred onto the substrate 153. The substrate 153 and the substrate 154 are preferably flexible. Accordingly, the flexibility of the authentication device 100B can be increased.

The adhesive layer 150 is provided on the outer side of the substrate 153. The authentication device 100B can be fixed to an object with the adhesive layer 150.

The inorganic insulating film that can be used as the insulating layer 211, the insulating layer 213, and the insulating layer 215 can be used as the insulating layer 212.

Providing the protective layer 195 covering the light-receiving element 110 and the light-emitting element 190 can inhibit entry of impurities such as water into the light-receiving element 110 and the light-emitting element 190, so that the reliability of the light-receiving element 110 and the light-emitting element 190 can be increased.

In the region 228 in the vicinity of an end portion of the authentication device 100B, the insulating layer 215 and the protective layer 195 are preferably in contact with each other through an opening in the insulating layer 214. In particular, the inorganic insulating film included in the insulating layer 215 and the inorganic insulating film included in the protective layer 195 are preferably in contact with each other. Thus, entry of impurities from the outside into the authentication device 100B through the organic insulating film can be inhibited. Thus, the reliability of the authentication device 100B can be increased.

The protective layer 195 may have a stacked-layer structure of an organic insulating film and an inorganic insulating film. In that case, an end portion of the inorganic insulating film preferably extends beyond an end portion of the organic insulating film.

[Authentication Device 100C]

FIG. 19A illustrates a cross-sectional view of an authentication device 100C.

The authentication device 100C differs from the authentication device 100B in the structure of the transistor.

The authentication device 100C includes the transistor 208, the transistor 209, and a transistor 210 over the substrate 151.

Each of the transistor 208, the transistor 209, and the transistor and 210 includes the conductive layer 221 functioning as a gate, the insulating layer 211 functioning as a gate insulating layer, a semiconductor layer including a channel formation region 231i and a pair of low-resistance regions 231n, the conductive layer 222a connected to one of the low-resistance regions 231n, the conductive layer 222b connected to the other low-resistance region 231n, an insulating layer 225 functioning as a gate insulating layer, the conductive layer 223 functioning as a gate, and the insulating layer 215 covering the conductive layer 223. The insulating layer 211 is positioned between the conductive layer 221 and the channel formation region 231i. The insulating layer 225 is positioned between the conductive layer 223 and the channel formation region 231i.

The conductive layer 222a and the conductive layer 222b are each connected to the corresponding low-resistance region 231n through openings provided in the insulating layer 225 and the insulating layer 215. One of the conductive layer 222a and the conductive layer 222b serves as a source, and the other serves as a drain.

The pixel electrode 191 of the light-emitting element 190 is electrically connected to one of the pair of low-resistance regions 231n of the transistor 208 through the conductive layer 222b.

The pixel electrode 111 of the light-receiving element 110 is electrically connected to the other of the pair of low-resistance regions 231n of the transistor 209 through the conductive layer 222b.

In each of the transistor 208, the transistor 209, and the transistor 210 illustrated in FIG. 19A, an example in which the insulating layer 225 covers a top surface and a side surface of the semiconductor layer is described. Meanwhile, in a transistor 202 illustrated in FIG. 19B, the insulating layer 225 overlaps with the channel formation region 231i of the semiconductor layer 231 and does not overlap with the low-resistance regions 231n. The structure illustrated in FIG. 19B is obtained by forming the insulating layer 225 with the conductive layer 223 as a mask, for example. In FIG. 19B, the insulating layer 215 is provided to cover the insulating layer 225 and the conductive layer 223, and the conductive layer 222a and the conductive layer 222b are connected to the low-resistance regions 231n through the openings in the insulating layer 215. Furthermore, an insulating layer 218 covering the transistor 202 may be provided.

[Metal Oxide]

A metal oxide that can be used for the semiconductor layer will be described below.

Note that in this specification and the like, a metal oxide containing nitrogen is also collectively referred to as a metal oxide in some cases. A metal oxide containing nitrogen may be referred to as a metal oxynitride. For example, a metal oxide containing nitrogen, such as zinc oxynitride (ZnON), may be used for the semiconductor layer.

A metal oxide with a low carrier concentration is preferably used for the semiconductor layer. In order to reduce the carrier concentration of the metal oxide, the concentration of impurities in the metal oxide is reduced so that the density of defect states can be reduced. In this specification and the like, a state with a low impurity concentration and a low density of defect states is referred to as a highly purified intrinsic or substantially highly purified intrinsic state. As examples of the impurities in the metal oxide, hydrogen, nitrogen, alkali metal, alkaline earth metal, iron, nickel, silicon, and the like are given.

In particular, hydrogen contained in the metal oxide reacts with oxygen bonded to a metal atom to be water, and thus forms oxygen vacancies in the metal oxide in some cases. If the channel formation region in the metal oxide includes oxygen vacancies, the transistor sometimes has normally-on characteristics. In some cases, a defect that is an oxygen vacancy into which hydrogen enters functions as a donor and generates an electron serving as a carrier. In other cases, bonding of part of hydrogen to oxygen bonded to a metal atom generates electrons serving as carriers. Thus, a transistor using a metal oxide containing much hydrogen is likely to have normally-on characteristics.

A defect in which hydrogen has entered an oxygen vacancy can function as a donor of the metal oxide. However, it is difficult to evaluate the defects quantitatively. Thus, the metal oxide is evaluated by carrier concentration, not by donor concentration, in some cases. Therefore, in this specification and the like, the carrier concentration assuming the state where an electric field is not applied is sometimes used, instead of the donor concentration, as the parameter of the metal oxide. That is, "carrier concentration" in this specification and the like can be replaced with "donor concentration" in some cases.

Therefore, hydrogen in the metal oxide is preferably reduced as much as possible. Specifically, the hydrogen concentration of the metal oxide, which is measured by secondary ion mass spectrometry (SIMS), is lower than $1\times10^{20}$ atoms/cm$^3$, preferably lower than $1\times10^{19}$ atoms/cm$^3$, further preferably lower than $5\times10^{18}$ atoms/cm$^3$, still further preferably lower than $1\times10^{18}$ atoms/cm$^3$. When a metal oxide with a sufficiently low concentration of impurities such as hydrogen is used for a channel formation region of a transistor, the transistor can have stable electrical characteristics.

The carrier concentration of the metal oxide in the channel formation region is preferably lower than or equal to $1\times10^{18}$ cm$^{-3}$, further preferably lower than $1\times10^{17}$ cm$^{-3}$, still further preferably lower than $1\times10^{16}$ cm$^{-3}$, yet further preferably lower than $1\times10^{13}$ cm$^{-3}$, and yet still further preferably lower than $1\times10^{12}$ cm$^{-3}$. Note that the lower limit of the carrier concentration of the metal oxide in the channel formation region is not particularly limited and can be, for example, $1\times10^{-9}$ cm$^3$.

Note that in this specification and the like, CAAC (c-axis aligned crystal) and CAC (Cloud-Aligned Composite) might be stated. Note that CAAC refers to an example of a crystal structure, and CAC refers to an example of a function or a material composition.

For example, a CAC (Cloud-Aligned Composite)-OS can be used for the semiconductor layer.

A CAC-OS or a CAC-metal oxide has a conducting function in part of the material and has an insulating function in another part of the material; as a whole, the CAC-OS or the CAC-metal oxide has a function of a semiconductor. Note that in the case where the CAC-OS or the CAC-metal oxide is used in a channel formation region of a transistor, the conducting function is a function that allows electrons (or holes) serving as carriers to flow, and the insulating function is a function that does not allow electrons serving as carriers to flow. By the complementary action of the conducting function and the insulating function, a switching function (On/Off function) can be given to the CAC-OS or the CAC-metal oxide. In the CAC-OS or the CAC-metal oxide, separation of the functions can maximize each function.

Furthermore, the CAC-OS or the CAC-metal oxide includes conductive regions and insulating regions. The conductive regions have the above-described conducting function, and the insulating regions have the above-described insulating function. Furthermore, in some cases, the conductive regions and the insulating regions in the material are separated at the nanoparticle level. Furthermore, in some cases, the conductive regions and the insulating regions are unevenly distributed in the material. Furthermore, in some cases, the conductive regions are observed to be coupled in a cloud-like manner with their boundaries blurred.

Furthermore, in the CAC-OS or the CAC-metal oxide, the conductive regions and the insulating regions each have a size greater than or equal to 0.5 nm and less than or equal to 10 nm, preferably greater than or equal to 0.5 nm and less than or equal to 3 nm, and are dispersed in the material, in some cases.

Furthermore, the CAC-OS or the CAC-metal oxide includes components having different bandgaps. For example, the CAC-OS or the CAC-metal oxide includes a component having a wide gap due to the insulating region and a component having a narrow gap due to the conductive region. In the case of the structure, when carriers flow, carriers mainly flow in the component having a narrow gap. Furthermore, the component having a narrow gap complements the component having a wide gap, and carriers also flow in the component having a wide gap in conjunction with the component having a narrow gap. Therefore, in the case where the above-described CAC-OS or CAC-metal oxide is used in a channel formation region of a transistor, high current driving capability in an on state of the transistor, that is, a high on-state current and high field-effect mobility can be obtained.

In other words, the CAC-OS or the CAC-metal oxide can also be referred to as a matrix composite or a metal matrix composite.

Oxide semiconductors (metal oxides) can be classified into a single crystal oxide semiconductor and a non-single-crystal oxide semiconductor. Examples of a non-single-crystal oxide semiconductor include a CAAC-OS (c-axis aligned crystalline oxide semiconductor), a polycrystalline oxide semiconductor, an nc-OS (nanocrystalline oxide semiconductor), an amorphous-like oxide semiconductor (a-like OS), and an amorphous oxide semiconductor.

The CAAC-OS has c-axis alignment, a plurality of nanocrystals are connected in the a-b plane direction, and its crystal structure has distortion. Note that the distortion refers to a portion where the direction of a lattice arrangement changes between a region with a regular lattice arrangement and another region with a regular lattice arrangement in a region where the plurality of nanocrystals are connected.

The nanocrystal is basically a hexagon but is not always a regular hexagon and is a non-regular hexagon in some cases. Furthermore, a pentagonal or heptagonal lattice arrangement, for example, is included in the distortion in some cases. Note that it is difficult to observe a clear crystal grain boundary (also referred to as grain boundary) even in the vicinity of distortion in the CAAC-OS. That is, formation of a crystal grain boundary is found to be inhibited by the distortion of a lattice arrangement. This is because the CAAC-OS can tolerate distortion owing to a low density of arrangement of oxygen atoms in the a-b plane direction, an interatomic bond length changed by substitution of a metal element, and the like.

Furthermore, the CAAC-OS tends to have a layered crystal structure (also referred to as a layered structure) in which a layer containing indium and oxygen (hereinafter, In layer) and a layer containing the element M, zinc, and oxygen (hereinafter, (M, Zn) layer) are stacked. Note that indium and the element M can be replaced with each other, and when the element M in the (M, Zn) layer is replaced with indium, the layer can also be referred to as an (In, M, Zn) layer. Furthermore, when indium in the In layer is replaced with the element M, the layer can be referred to as an (In, M) layer.

The CAAC-OS is a metal oxide with high crystallinity. On the other hand, a clear crystal grain boundary cannot be observed in the CAAC-OS; thus, it can be said that a reduction in electron mobility due to the crystal grain boundary is less likely to occur. Entry of impurities, formation of defects, or the like might decrease the crystallinity of a metal oxide; thus, it can be said that the CAAC-OS is a metal oxide that has small amounts of impurities and defects (e.g., oxygen vacancies (also referred to as $V_O$)). Thus, a metal oxide including a CAAC-OS is physically stable. Therefore, the metal oxide including a CAAC-OS is resistant to heat and has high reliability.

In the nc-OS, a microscopic region (e.g., a region with a size greater than or equal to 1 nm and less than or equal to 10 nm, in particular, a region with a size greater than or equal to 1 nm and less than or equal to 3 nm) has a periodic atomic arrangement. Furthermore, there is no regularity of crystal orientation between different nanocrystals in the nc-OS. Thus, the orientation in the whole film is not observed. Accordingly, the nc-OS cannot be distinguished from an a-like OS or an amorphous oxide semiconductor by some analysis methods.

Note that indium-gallium-zinc oxide (hereinafter referred to as IGZO) that is a kind of metal oxide containing indium, gallium, and zinc has a stable structure in some cases by being formed of the above-described nanocrystals. In particular, crystals of IGZO tend not to grow in the air and thus, a stable structure is obtained when IGZO is formed of smaller crystals (e.g., the above-described nanocrystals) rather than larger crystals (here, crystals with a size of several millimeters or several centimeters).

An a-like OS is a metal oxide having a structure between those of the nc-OS and an amorphous oxide semiconductor. The a-like OS includes a void or a low-density region. That is, the a-like OS has low crystallinity as compared with the nc-OS and the CAAC-OS.

An oxide semiconductor (metal oxide) can have various structures which show different properties. Two or more of the amorphous oxide semiconductor, the polycrystalline oxide semiconductor, the a-like OS, the nc-OS, and the CAAC-OS may be included in an oxide semiconductor of one embodiment of the present invention.

A metal oxide film that functions as a semiconductor layer can be deposited using either or both of an inert gas and an oxygen gas. Note that there is no particular limitation on the flow rate ratio of oxygen (the partial pressure of oxygen) at the time of depositing the metal oxide film. However, to obtain a transistor having high field-effect mobility, the flow rate ratio of oxygen (the partial pressure of oxygen) at the time of depositing the metal oxide film is preferably higher than or equal to 0% and lower than or equal to 30%, further preferably higher than or equal to 5% and lower than or equal to 30%, still further preferably higher than or equal to 7% and lower than or equal to 15%.

The energy gap of the metal oxide is preferably 2 eV or more, further preferably 2.5 eV or more, still further preferably 3 eV or more. With use of a metal oxide having such a wide energy gap, the off-state current of the transistor can be reduced.

The substrate temperature during the deposition of the metal oxide film is preferably lower than or equal to 350° C., further preferably higher than or equal to room temperature and lower than or equal to 200° C., still further preferably higher than or equal to room temperature and lower than or equal to 130° C. The substrate temperature during the deposition of the metal oxide film is preferably room temperature because productivity can be increased.

The metal oxide film can be formed by a sputtering method. Alternatively, a PLD method, a PECVD method, a thermal CVD method, an ALD method, or a vacuum evaporation method, for example, may be used.

As described above, the authentication device of this embodiment includes a light-receiving element and a light-emitting element in an imaging portion, and the imaging portion has both a function of emitting light and a function of sensing light. Thus, the size and weight of an electronic device can be reduced as compared to the case where a sensor is provided outside an imaging portion or outside an authentication device. Moreover, an electronic device having more functions can be obtained by a combination of the authentication device of this embodiment and a sensor provided outside the imaging portion or outside the authentication device.

In the light-receiving element, at least one of the layers other than the active layer can be common to the layer in the light-emitting element (the EL element). Furthermore, in the light-receiving element, all the layers other than the active layer can be common to the layers in the light-emitting element (the EL element). With only the addition of the step of depositing the active layer to the manufacturing process of the light-emitting element, the light-emitting element and the light-receiving element can be formed over one substrate, for example. In the light-receiving element and the light-emitting element, their pixel electrodes can be formed using the same material in the same step, and their common electrodes can be formed using the same material in the same step. When a circuit electrically connected to the light-receiving element and a circuit electrically connected to the light-emitting element are formed using the same material in the same process, the manufacturing process of the authentication device can be simplified. In such a manner, an authentication device that incorporates a light-receiving element and is highly convenient can be manufactured without complicated steps.

The authentication device of this embodiment includes a colored layer between the light-receiving element and the light-emitting element. A bank that electrically isolates the light-receiving element and the light-emitting element may also function as the colored layer. The colored layer can absorb stray light in the authentication device, which increases the sensitivity of a sensor using the light-receiving element.

At least part of the structure examples, the drawings corresponding thereto, and the like exemplified in this embodiment can be implemented in combination with the other structure examples, the other drawings, and the like as appropriate.

At least part of this embodiment can be implemented in combination with the other embodiments described in this specification as appropriate.

REFERENCE NUMERALS

BM: light-blocking layer, T1: period, T2: period, T3: period, T4: period, 10: pixel circuit, 11: light-emitting element, 12: infrared light, 13: light-receiving element, 14: infrared light, 20: imaging device, 21: pixel array, 22: circuit, 23: circuit, 24: circuit, 25: circuit, 26: circuit, 28: circuit, 41: transistor, 42: transistor, 51: substrate, 52: hand, 55: layer, 57: adhesive layer, 59: substrate, 61: vein, 63: backscattering light, 65: object, 80: authentication device, 80A: authentication device, 80B: authentication device, 80C: authentication device, 80D: authentication device, 80E: authentication device, 80F: authentication device, 81: imaging portion, 82: control portion, 83: memory portion, 84: program, 85: input/output portion, 86: authentication portion, 87: external driver circuit, 88: antenna, 91: door, 93: door knob, 95: electronic lock, 96: bolt, 97: door, 98: door knob, 100A: authentication device, 100B: authentication device, 100C: authentication device, 101: light-receiving element, 103: transistor, 104: transistor, 105: transistor, 106: transistor, 107: transistor, 108: capacitor, 109: resistor, 110: light-receiving element, 111: pixel electrode, 112: common layer, 113: active layer, 114: common layer, 115: common electrode, 121: wiring, 122: wiring, 123a: light, 123b: reflected light, 123c: light, 123d: reflected light, 126: wiring, 127: wiring, 128: wiring, 129: wiring, 130: wiring, 131: wiring, 132: wiring, 142: adhesive layer, 143: space, 150: adhesive layer, 151: substrate, 152: substrate, 153: substrate, 154: substrate, 155: adhesive layer, 162: pixel array, 164: circuit, 182: buffer layer, 184: buffer layer, 190: light-emitting element, 191: pixel electrode, 192: buffer layer, 193: light-emitting layer, 194: buffer layer, 195: protective layer, 201: transistor, 202: transistor, 205: transistor, 206: transistor, 208: transistor, 209: transistor, 210: transistor, 211: insulating layer, 212: insulating layer, 213: insulating layer, 214: insulating layer, 215: insulating layer, 216: bank, 217: bank, 218: insulating layer, 221: conductive layer, 222a: conductive layer, 222b: conductive layer, 223: conductive layer, 225: insulating layer, 228: region, 231: semiconductor layer, 23i: channel formation region, 231n: low-resistance region, 5700: automobile

The invention claimed is:

1. An imaging device comprising:
a substrate;
a pixel array; and
an adhesive layer,
wherein the substrate has flexibility,
wherein the pixel array is over a first surface of the substrate,
wherein the adhesive layer is on a second surface facing the first surface of the substrate,
wherein the pixel array comprises a light-receiving element and a light-emitting element,
wherein the light-receiving element is configured to sense infrared light,
wherein the light-receiving element comprises a first pixel electrode, a common layer, an active layer, and a common electrode,
wherein the light-emitting element is configured to emit infrared light,
wherein the light-emitting element comprises a second pixel electrode, the common layer, a light-emitting layer, and the common electrode,
wherein the active layer is over the first pixel electrode and the common layer,
wherein the active layer comprises a first organic compound,
wherein the light-emitting layer is over the second pixel electrode and the common layer,
wherein the light-emitting layer comprises a second organic compound different from the first organic compound, wherein the common layer is over the first pixel electrode and the second pixel electrode, and wherein the common electrode comprises a portion overlapping the first pixel electrode with the active layer therebetween and a portion overlapping with the second pixel electrode with the light-emitting layer therebetween.

2. An imaging device comprising:
a substrate;
a pixel array; and
an adhesive layer,
wherein the substrate has flexibility,
wherein the pixel array is over a first surface of the substrate,
wherein the adhesive layer is on a second surface facing the first surface of the substrate,
wherein the pixel array comprises a light-receiving element and a light-emitting element,
wherein the light-receiving element is configured to sense infrared light,
wherein the light-receiving element comprises a first pixel electrode, a common layer, an active layer, a first buffer layer, and a common electrode,
wherein the light-emitting element is configured to emit infrared light,
wherein the light-emitting element comprises a second pixel electrode, the common layer, a light-emitting layer, a second buffer layer, and the common electrode,
wherein the active layer is over the first pixel electrode,
wherein the active layer comprises a first organic compound,
wherein the light-emitting layer is over the second pixel electrode,
wherein the light-emitting layer comprises a second organic compound different from the first organic compound,
wherein the common layer is over the first pixel electrode and the second pixel electrode, and
wherein the common electrode comprises a portion overlapping the first pixel electrode with the common layer and the active layer therebetween and a portion overlapping with the second pixel electrode with the common layer and the light-emitting layer therebetween.

3. The imaging device according to claim 1, wherein the pixel array comprises at least one of a transistor comprising a metal oxide in a channel formation region and a transistor comprising silicon in a channel formation region.

4. An authentication device comprising:
the imaging device described in claim 1;
a control portion;
a memory portion; and
an input/output portion,
wherein the control portion, the memory portion, and the input/output portion are over the first surface,
wherein the imaging device is configured to capture an image,
wherein the memory portion is configured to store a registered image,
wherein the control portion is configured to compare the image and the registered image,
wherein the input/output portion comprises an antenna,
wherein the input/output portion is configured to output a result of the comparison to the outside, and
wherein the input/output portion is configured to receive power wirelessly.

5. The authentication device according to claim 4, further comprising:
an external driver circuit,
wherein the external driver circuit is not in contact with the substrate, and
wherein the input/output portion is configured to output a result of the comparison to the external driver circuit.

6. The imaging device according to claim 2, wherein the pixel array comprises at least one of a transistor comprising a metal oxide in a channel formation region and a transistor comprising silicon in a channel formation region.

7. An authentication device comprising:
the imaging device described in claim 2;
a control portion;
a memory portion; and
an input/output portion,
wherein the control portion, the memory portion, and the input/output portion are over the first surface,
wherein the imaging device is configured to capture an image,
wherein the memory portion is configured to store a registered image,
wherein the control portion is configured to compare the image and the registered image,
wherein the input/output portion comprises an antenna,
wherein the input/output portion is configured to output a result of the comparison to the outside, and
wherein the input/output portion is configured to receive power wirelessly.

8. The authentication device according to claim 7, further comprising:
an external driver circuit,
wherein the external driver circuit is not in contact with the substrate, and
wherein the input/output portion is configured to output a result of the comparison to the external driver circuit.

* * * * *